United States Patent
Agejas-Chicharro et al.

(10) Patent No.: US 9,416,138 B2
(45) Date of Patent: Aug. 16, 2016

(54) BENZYL SULFONAMIDE COMPOUNDS USEFUL AS MOGAT-2 INHIBITORS

(71) Applicant: Eli Lilly and Company, Indianapolis, IN (US)

(72) Inventors: Francisco Javier Agejas-Chicharro, Madrid (ES); Nuria Diaz Buezo, Madrid (ES); Joseph Michael Gruber, Brownsburg, IN (US); Douglas Richard Stack, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/438,435

(22) PCT Filed: Oct. 30, 2013

(86) PCT No.: PCT/US2013/067466
§ 371 (c)(1),
(2) Date: Apr. 24, 2015

(87) PCT Pub. No.: WO2014/074365
PCT Pub. Date: May 15, 2014

(65) Prior Publication Data
US 2015/0284404 A1 Oct. 8, 2015

Related U.S. Application Data

(60) Provisional application No. 61/748,935, filed on Jan. 4, 2013.

(30) Foreign Application Priority Data

Nov. 6, 2012 (EP) ..................................... 12382431

(51) Int. Cl.
| | |
|---|---|
| C07D 207/00 | (2006.01) |
| C07D 491/056 | (2006.01) |
| C07D 273/00 | (2006.01) |
| C07D 309/04 | (2006.01) |
| C07D 311/58 | (2006.01) |
| C07D 311/76 | (2006.01) |
| C07D 217/24 | (2006.01) |
| C07D 319/12 | (2006.01) |
| C07D 319/20 | (2006.01) |
| C07D 263/58 | (2006.01) |
| C07D 491/052 | (2006.01) |
| C07D 265/30 | (2006.01) |
| C07D 265/36 | (2006.01) |
| C07D 207/14 | (2006.01) |
| C07D 307/22 | (2006.01) |
| C07D 307/79 | (2006.01) |
| C07D 309/00 | (2006.01) |
| C07D 311/00 | (2006.01) |
| C07D 217/00 | (2006.01) |

(Continued)

(52) U.S. Cl.
CPC .......... *C07D 491/056* (2013.01); *C07D 207/00* (2013.01); *C07D 207/14* (2013.01); *C07D 217/00* (2013.01); *C07D 217/24* (2013.01); *C07D 263/00* (2013.01); *C07D 263/58* (2013.01); *C07D 265/30* (2013.01); *C07D 265/36* (2013.01); *C07D 273/00* (2013.01); *C07D 307/00* (2013.01); *C07D 307/22* (2013.01); *C07D 307/79* (2013.01); *C07D 307/87* (2013.01); *C07D 309/00* (2013.01); *C07D 309/04* (2013.01); *C07D 311/00* (2013.01); *C07D 311/58* (2013.01); *C07D 311/76* (2013.01); *C07D 319/00* (2013.01); *C07D 319/12* (2013.01); *C07D 319/20* (2013.01); *C07D 491/052* (2013.01)

(58) Field of Classification Search
CPC ....................................................... C07D 207/00
See application file for complete search history.

(56) References Cited

U.S. PATENT DOCUMENTS

| | | | |
|---|---|---|---|
| 6,303,816 | B1 | 10/2001 | Arnold et al. |
| 8,507,493 | B2 | 8/2013 | Peddi et al. |

(Continued)

FOREIGN PATENT DOCUMENTS

| | | |
|---|---|---|
| EP | 1655283 | 11/2004 |
| EP | 1659113 | 11/2004 |

(Continued)

OTHER PUBLICATIONS

Take "Pharmacological Inhibition of Monoacylglycerol O-Acyltransferase 2 Improves Hyperlipidemia, Obesity, and Diabetes by Change in Intestinal Fat Utilization" PLoS One (2016) 11(3): e0150976.*

(Continued)

*Primary Examiner* — David K. O'Dell
(74) *Attorney, Agent, or Firm* — James B. Myers

(57) ABSTRACT

The present invention provides compounds of Formula I. Wherein R1, L, and A are as described herein, or a pharmaceutical salt thereof, processes for preparing the compounds, and methods of treating a condition, such as hypertriglyceridemia, using the compounds.

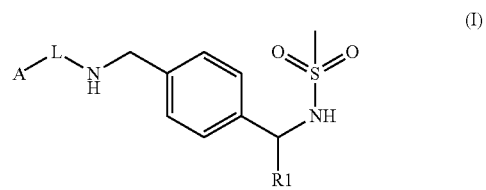

24 Claims, No Drawings

(51) Int. Cl.
  *C07D 319/00* (2006.01)
  *C07D 263/00* (2006.01)
  *C07D 307/00* (2006.01)
  *C07D 307/87* (2006.01)

(56) References Cited

U.S. PATENT DOCUMENTS

| | | | |
|---|---|---|---|
| 8,575,352 | B2 | 11/2013 | Fernandez et al. |
| 2011/0275647 | A1 | 11/2011 | Arakawa et al. |
| 2014/0371269 | A1 | 12/2014 | Fernandez |
| 2015/0005305 | A1 | 1/2015 | Gonzalez-Garcia |

FOREIGN PATENT DOCUMENTS

| | | |
|---|---|---|
| EP | 2078719 | 9/2007 |
| WO | 2013/112323 | 1/2008 |
| WO | 2013/116065 | 8/2008 |

OTHER PUBLICATIONS

Yen, et al., "MAT2, a Monoacylglycerol Acyltransferase Expressed in the Small Intestine," The Journal of Biological Chemistry, vol. 278, No. 20, Issue of May 16, pp. 18532-18537 (2003).

Hall, et al., "Evidence for regulated monoacylglycerol acyltransferase expression and activity in human liver," Journal of Lipid Research, vol. 53, pp. 990-999 (2012).

Cao, et al., "A Predominant Role of Acyl-CoA:monoacylglycerol Acyltransferase-2 in Dietary Fat Absorption Implicated by Tissue Distribution, Subcellular Localization, and Up-regulation by High Fat Diet," The Journal of Biological Chemistry, vol. 279, No. 18, Issue of Apr. 30, pp. 18878-18886 (2004).

Yen, et al., "Deficiency of the intestinal enzyme acyl CoA:monoacylglycerol acyltransferase-2 protects mice from metabolic disorders induced by high-fat feeding," Nature Medicine, vol. 15, No. 4, pp. 442-446 (2009).

* cited by examiner

BENZYL SULFONAMIDE COMPOUNDS USEFUL AS MOGAT-2 INHIBITORS

Ingestion of excess dietary fat is a leading cause of diet induced obesity and can have a profound detrimental effect on a people's health. More than 90% of dietary fat for humans is triacylglycerol (or triglyceride), which is nearly completely absorbed by the small intestine. The enzyme acyl CoA: monoacylglycerol acytransferase-2 (MoGAT-2) is believed to play an important role in the absorption of dietary fat in the small intestines. It has been demonstrated that MoGAT-2 deficient mice when fed a high fat diet are protected against developing obesity, glucose intolerance, hypercholesterolemia and developing a fatty liver. Further, it has also been shown that MoGAT-2 deficient mice exhibit lower plasma triacylglycerol levels after a dietary olive oil challenge. (Yen, et al, *Nat. Med.* 2009, 15(4), 442-446.)

There is a need for additional drugs for the treatments of hypertriglyceridemia. There is also a need for new inhibitors of the MoGAT-2 receptor. The present invention addresses one or more of these needs by providing alternative compounds and treatment methods, which may be suitable for the treatment hypertriglyceridemia.

The present invention provides a compound of Formula I below:

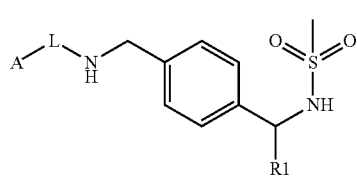

wherein: L is selected from: —CH$_2$— and —CH$_2$CH$_2$—; R1 is selected from: —CH$_3$ and —CF$_3$; and A is selected from:

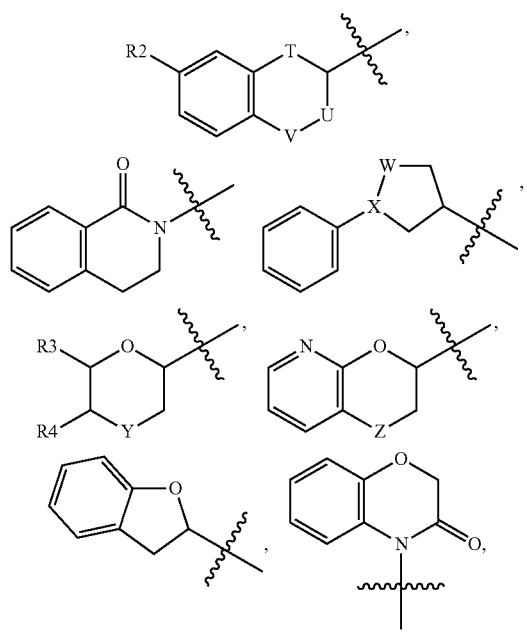

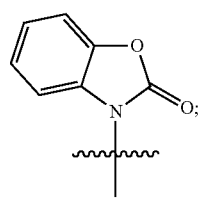

wherein for A: T is selected from: CH$_2$, NH, and O; U is selected from: CH$_2$, NH, and O; V is selected from: CH$_2$, C=O, NH, N—CH$_3$, and O, provided that at least one but not all of T, U, and V are CH$_2$, and when U is O then each T and V are other than O or N; W is selected from CH$_2$ and O; X is selected from: CH and N; provided that when W is CH$_2$, X is N and when W is O, X is CH; Y is selected from CH$_2$, N—C$_6$H$_5$, and O; Z is selected from CH$_2$ and O; R2 is selected from H and halogen; R3 is selected from H, cyclopropyl, and phenyl; R4 is selected from H and phenyl, wherein ⋎ indicates the bond attaching A to L. The present invention provides pharmaceutically acceptable salts of the compound of Formula I.

In one embodiment the compounds of Formula I have the stereochemistry illustrated below:

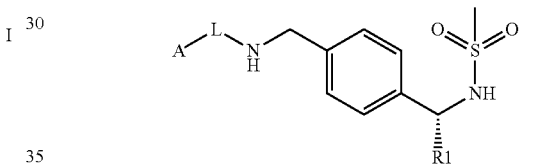

wherein R1, L, A, T, U, V, W, X, Y, Z, R2, R3, and R4 are as described above and pharmaceutically acceptable salts thereof.

The present invention provides compounds of Formula I where L is preferably is

—CH$_2$— and pharmaceutically acceptable salts thereof.

In one embodiment compounds of Formula I, R1 is —CH$_3$; in another embodiment R1 is —CF$_3$. The present invention provides pharmaceutically acceptable salts of both embodiments.

The present invention provides a compound of Formula I, wherein A is preferably is selected from:

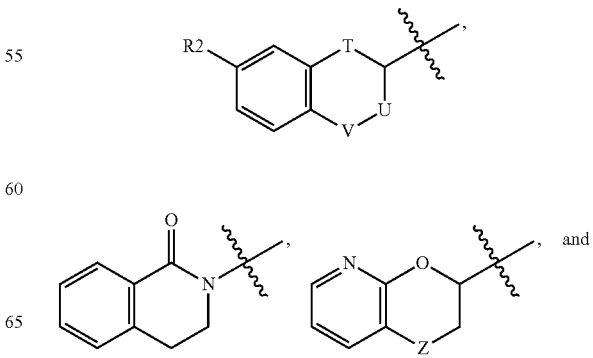

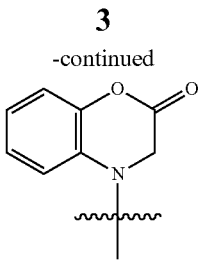

or a pharmaceutically acceptable salt thereof.

The present invention provides a compounds of Formula I wherein A is

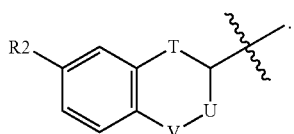

Preferably T is O or N; U is CH₂; V is O or N.

In one embodiment T and V are both O.

In another embodiment, T is O and V is N.

In another embodiment T and V are both CH₂, and U is O.

The present invention n provides compounds of Formula I wherein R2 is preferably selected from: H and F; more preferably R2 is H.

The present invention provides compounds of Formula I wherein A is selected from:

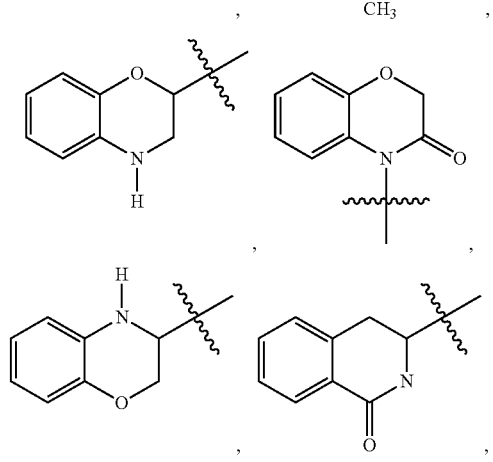

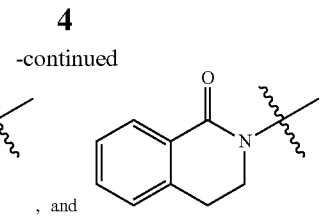

, and or a pharmaceutically acceptable salt thereof.

The present invention provides a compound of Formula I wherein A is selected from:

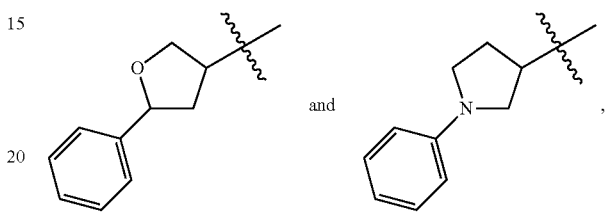

and

, or a pharmaceutically salt thereof.

The present invention provides a compound of Formula I, wherein A is selected from:

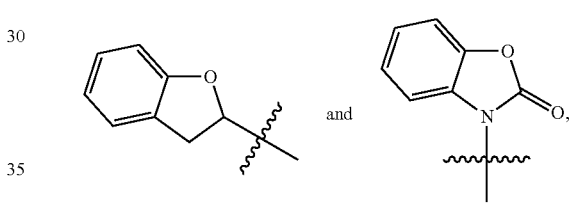

and

, or a pharmaceutically salt thereof.

The present invention provides a compound of Formula I, wherein A is selected from:

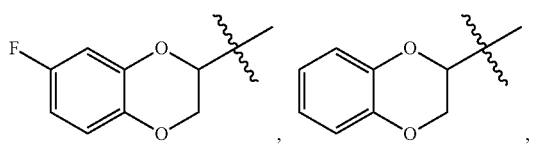

, and

, or a pharmaceutically salt thereof.

The present invention provides a compound of Formula I, wherein A is selected from:

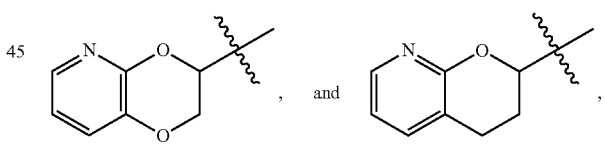

, and

, or a pharmaceutically salt thereof.

The present invention provides a compound of Formula I, wherein A is selected from:

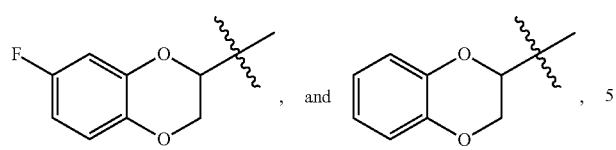, and
or a pharmaceutically salt thereof.
The present invention provides a compound of Formula I
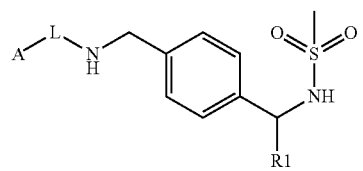
wherein L is selected from: —CH₂—, and —CH₂CH₂—; R1 is selected from: —CH₃ and —CF₃; wherein A is selected from:
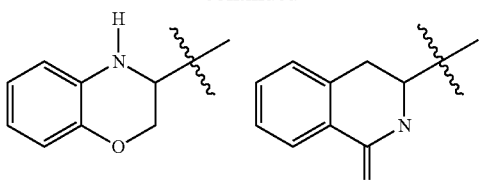,
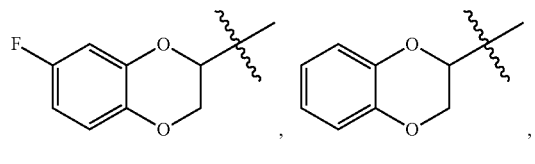,
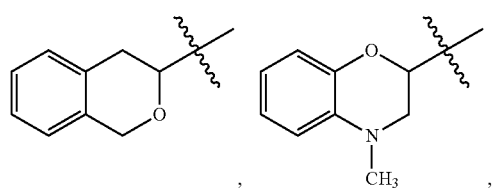,
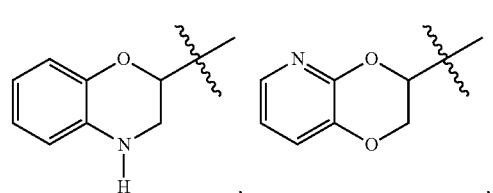,
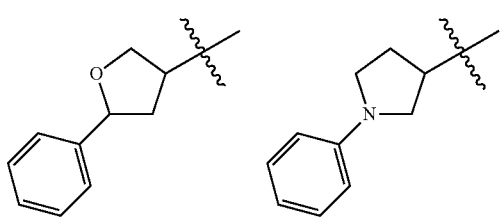,
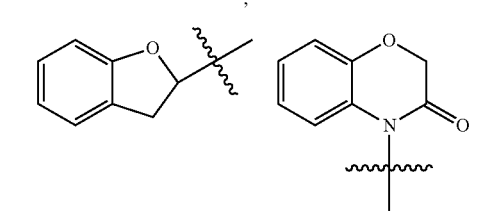,
-continued
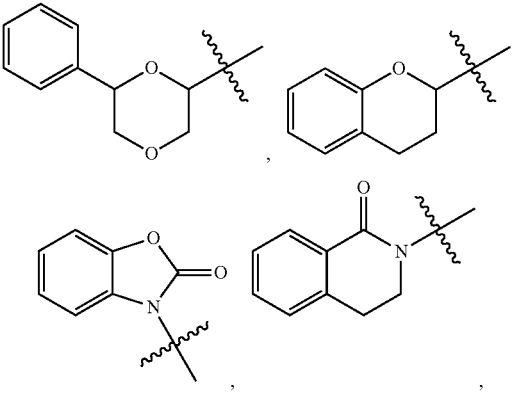,
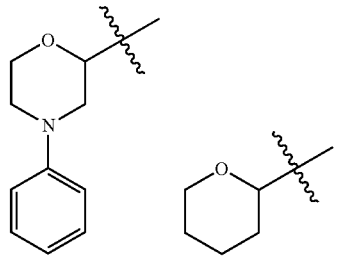,
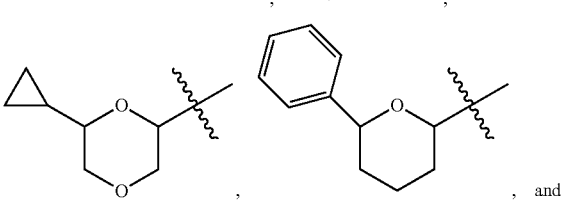,
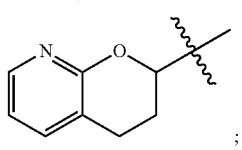, and
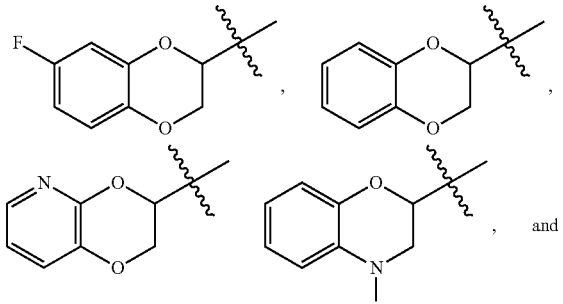;
or a pharmaceutically acceptable salt thereof.
The present invention provides a compound of Formula I, wherein A is:

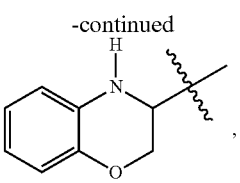

or a pharmaceutically salt thereof.

The present invention provides a compound which is:

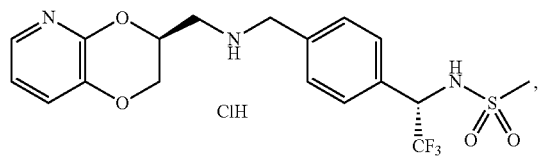

or a pharmaceutically salt thereof.

The present invention provides a compound which is:

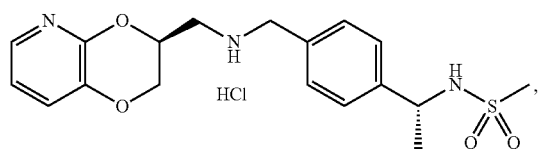 [SMILES: C[C@@H](NS(C)(=O)=O)c1ccc(CNC[C@H]2COc3cccnc3O2)cc1 ; Cl]

or a pharmaceutically salt thereof.

The present invention provides a pharmaceutical composition comprising a compound according to Formula I above, or a pharmaceutically acceptable salt thereof, and at least one of a pharmaceutically acceptable carrier, diluent, or excipient.

The present invention provides a method of treating a patient in need of treatment for hypertriglyceridemia. The method comprises administering to the patient an effective amount of a compound, according to Formula I above or a pharmaceutically acceptable salt thereof.

The present invention provides a method of treating a patient in need of treatment for hypertriglyceridemia. The method comprises administering to the patient an effective amount of a pharmaceutical composition comprising a compound according to Formula I above, or a pharmaceutically acceptable salt thereof, and at least one of a pharmaceutically acceptable carrier, diluent, or excipient.

The present invention provides a compound according to Formula I, or a pharmaceutically acceptable salt thereof, for use in therapy.

The present invention provides a compound, according to Formula I, or a pharmaceutically acceptable salt thereof, for use in the treatment of hypertriglyceridemia.

The present invention provides for the use of a compound according to Formula I, or a pharmaceutically acceptable salt thereof, for the manufacture of a medicament to treat hypertriglyceridemia.

The term "pharmaceutically-acceptable salt" refers a salt of the compound of the invention considered to be acceptable for clinical and/or veterinary use. Pharmaceutically acceptable salts and common methodology for preparing them are known in the art. See for example, P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

As used herein patient in need of treatment refers to a mammal, preferably a human; a companion animal, such as a dog or cat; or a fowl.

Pharmaceutical formulations of the present invention may be prepared by procedures known in the art using known ingredients including carriers, diluents and/or excipients. The term "pharmaceutically acceptable carrier, diluent, or excipient" as used herein refers to one or more carriers, diluents, and excipients that are compatible with the other ingredients of the formulation and not deleterious to a patient. Pharmaceutical compositions and processes for their preparation are known in the art and examples can be found in Remington, "The Science and Practice of Pharmacy" (A. Gennaro, et al. eds. 19$^{th}$ ed. Mack Publishing Co.) Non-limiting examples of pharmaceutically acceptable carriers, excipients, and diluents are suitable for such formulations include the following: starch, sugars, mannitol, and silica derivatives; binding agents such as carboxymethyl cellulose and other cellulose derivatives, alginates, gelatin, and polyvinyl-pyrrolidone.

Unless noted to the contrary, the compounds illustrated herein are named and numbered using either ACDLABS or Symyx Draw 3.2.

General Chemistry

As used herein, the following terms have the meanings indicated: "ACN" refers to acetonitrile; "DCM" refers to dichloromethane; "DEA" refers to diethylamine; "DMEA" refers to dimethylethylamine; "DMF" refers to dimethylformamide; "ee" refers to enantiomeric excess; "EtOAc" refers to ethyl acetate; "EtOH" refers to ethanol; "IPA" refers to isopropyl alcohol; IPA" refers to isopropyl amine; "Isomer 1" refers to the first eluting isomer under the conditions proscribed herein; "Isomer 2" refers to the second eluting isomer under the conditions proscribed herein; "LC/MS" refers to liquid chromatography followed by mass spectroscopy; "MeOH" refers to methanol; "MS" refers to mass spectroscopy; "NMR" refers to nuclear magnetic resonance; "Prep" refers to preparation; "SFC" refers to supercritical fluid chromatography; "THF" refers to tetrahydrofuran.

Scheme 1 illustrates the general synthesis of compound of Formula I.

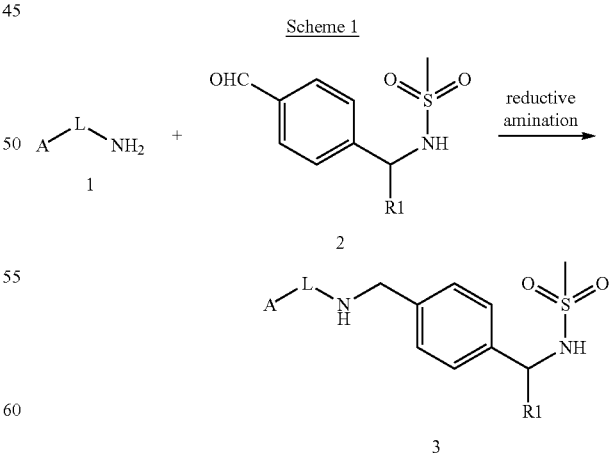

A substituted amine compound 1, which is either commercially available or synthesized by known literature methods, reacts with the aldehyde compound 2 under reductive amination conditions, which are also generally known to skilled artisans, to provide the compound of Formula 3. (See: Richard C. Larock, *Comprehensive Organic Transformations: a guide to functional group preparations*, 2$^{nd}$ edition, Page 835-846, Wiley-VCH, (1999)). More specifically, substituted amine compound 1 reacts with aldehyde compound 2 in the presence of a reducing agent, such as triacetoxyborohydride, and an acid, such as acetic acid, in dichloromethane (DCM) to provide the compound of Formula 3. Compounds of Formula 3 can be converted to a salt, for example with hydrochloric acid, to form the hydrochloride salt. Specific enantiomers or diasteriomers can be prepared by starting with the chiral aldehyde 2 having either an R or S configuration as desired.

PREPARATION 1

(N—Z)—N-[(4-Bromophenyl)methylene]-(R)-2-methyl-propane-2-sulfinamide

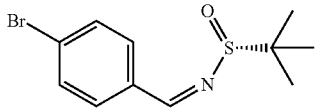

Add (R)-2-methylpropane-2-sulfinamide (40.5 g, 0.33 mol) portion-wise to a solution of 4-bromobenzaldehyde (65.57 g, 0.35 mol) in toluene (283 mL). Stir the mixture at ambient temperature for 15 minutes and then add sodium hydroxide (1.34 g, 0.33 mol). Stir the suspension at ambient temperature for 12 hours. Add sodium sulphate (16 g) and Celite® (16 g) and stir the suspension for 15 minutes. Filter and concentrate the filtrate under reduced pressure. Purify by silica gel chromatography eluting with hexane/EtOAc (100% to 70% hexane) to afford the title compound as a white solid (85.5 g, 88% yield). MS (m/z): 288 (M+1).

PREPARATION 2

N-[(1S)-1-(4-Bromophenyl)-2,2,2-trifluoro-ethyl]-(R)-2-methyl-propane-2-sulfinamide

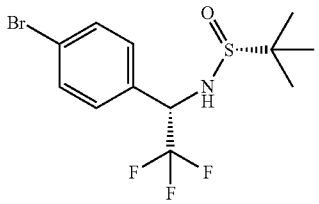 [SMILES: CC(C)(C)[S@@](=O)N[C@@H](c1ccc(Br)cc1)C(F)(F)F]

Add neat (trifluoromethyl)trimethylsilane (109 mL, 0.74 mol) to a stirred solution of tetrabutylammonium acetate (88 g, 0.29 mol) and (N—Z)—N-[(4-bromophenyl)methylene]-(R)-2-methyl-propane-2-sulfinamide (85 g, 0.29 mol) in DMF (1.2 L) at 0° C. Stir the mixture at 0-5° C. for 90 min Add a saturated aqueous ammonium chloride solution (1.2 L) and extract with EtOAc (4×400 mL). Combine the organic extracts; sequentially wash the extracts with water then brine (2×1 L); dry over MgSO$_4$; filter; and concentrate the filtrate under reduced pressure. Triturate the residue with hexane (200 mL) for 10 min; filter; and dry under reduced pressure to afford the title compound as a yellow solid (81 g, 76% yield, >98 de). MS (m/z): 358 (M+1).

PREPARATION 3

(1S)-1-(4-Bromophenyl)-2,2,2-trifluoroethanamine

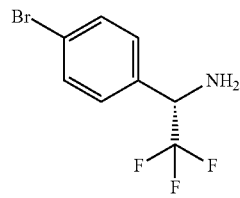 [SMILES: N[C@@H](c1ccc(Br)cc1)C(F)(F)F]

Add HCl (4 M in dioxane, 226 mL, 0.9 mol) to a suspension of N-[(1S)-1-(4-bromophenyl)-2,2,2-trifluoro-ethyl]-(R)-2-methyl-propane-2-sulfinamide (81 g, 0.23 mol) in MeOH (670 mL). Stir at ambient temperature for one h. Remove the solvent under reduced pressure and triturate the residue with methyl tert-butyl ether (200 mL) for 10 minutes to provide the HCl salt of the title compounds as a brown solid. Dissolve the salt in water and add 2N NaOH solution until the pH of the mixture is 10. Extract the mixture with methyl tert-butyl ether (3×500 mL). Wash the combined organic extracts with water, then brine (500 mL each); dry over, MgSO$_4$; filter; and concentrate the filtrate under reduced pressure to provide the title compound as a yellow solid (46 g, 80% yield, 98% ee). MS (m/z): 358 (M+1).

PREPARATION 4

N-[(1S)-1-(4-Bromophenyl)-2,2,2-trifluoro-ethyl] methanesulfonamide

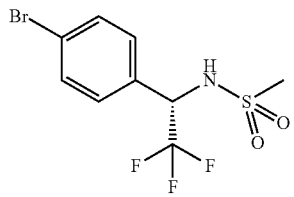 [SMILES: CS(=O)(=O)N[C@@H](c1ccc(Br)cc1)C(F)(F)F]

Add methanesulfonyl chloride (16.42 mL, 0.21 mol) dropwise to a mixture of (1S)-1-(4-bromophenyl)-2,2,2-trifluoroethanamine (49 g, 0.19 mol), 4-dimethylaminopyridine (1.18 g, 9.0 mmol), 2,6-lutidine (67 mL, 0.57 mol) in DCM (250 mL) at 0° C. Warm the mixture to ambient temperature and stir the mixture at that temperature for 20 h. Dilute the reaction mixture with DCM (300 mL) and wash it sequentially with aqueous HCl (2 M, 2×200 mL), water (250 mL), then brine (250 mL). Collect the organic phase; dry over MgSO$_4$; filter; and concentrate the filtrate under reduced pressure. Triturate the residue with hexane (200 mL) for 10 minutes;

filter; and dry the solid under reduced pressure to provide the title compound as a pale brown solid (60 g, 93% yield, 98% ee). MS (m/z): 332 (M+1).

PREPARATION 5

N-[(1S)-2,2,2-Trifluoro-1-(4-formylphenyl)ethyl]methanesulfonamide

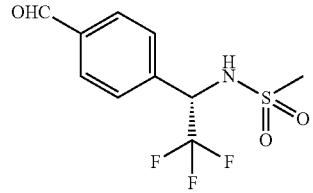 [SMILES: CS(=O)(=O)N[C@@H](c1ccc(C=O)cc1)C(F)(F)F]

Combine N-[(1S)-1-(4-bromophenyl)-2,2,2-trifluoroethyl]methanesulfonamide (30 g, 90 mmol), palladium(II) acetate (0.81 g, 3.6 mmol), butyldi-1-adamantylphosphine (3.89 g, 10.84 mmol) and tetramethylethylenediamine (10.50 g, 90 mmol) and toluene (1.5 mL) in a 2 L PARR reactor. Charge the reactor with synthesis gas (1:1 CO/$H_2$ at 75 psi) and then seal it. Heat to 95° C. and stir the reaction mixture for 16 hours. Cool the mixture; vent; and then open the reactor. Filter the mixture through Celite® and concentrate the filtrate under reduced pressure. Purify by silica gel chromatography eluting with hexane/EtOAc (8:2 to 1:1) to afford the title compound (22.8 g, 90%, 80% ee). Enrich the chiral purity by using a chiral column: Chiralpak AS-H (2.1×25 cm, 5 uM) $CO_2$/EtOH (9:1) to provide the title compound (19 g, 75% yield, 98% ee). MS (m/z): 282 (M+1).

PREPARATION 6

N-[(1R)-1-(4-Bromophenyl)ethyl]methanesulfonamide

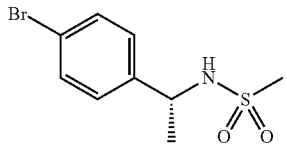

Add methanesulfonyl chloride (13.44 mL, 0.17 mmol) to a mixture of (1R)-1-(4-bromophenyl)ethanamine (25 g, 0.12 mol) and triethylamine (51 mL, 0.36 mol) in DCM (250 mL) at 0° C. Warm to ambient temperature and stir for 2.5 hours. Wash the reaction mixture with aqueous HCl (2 M, 100 ml). Sequentially wash the organic phase with water and then brine (2×100 mL). Dry the organic phase over anhydrous $Na_2SO_4$; filter; and concentrate the filtrate under reduced pressure to provide a residue. Triturate the residue with hexane (150 mL); filter; and dry under reduced pressure to afford the title compound as a yellow solid (33.24 g, 96%, ee>98%). MS (m/z): 278 (M+1).

PREPARATION 7

N-[(1R)-1-(4-Formylphenyl)ethyl]methanesulfonamide

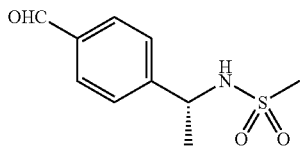

Combine N-[(1R)-1-(4-bromophenyl)ethyl]-methanesulfonamide (10 g, 35 mmol), (1,1'-bis(diphenylphosphino)-ferrocene)palladium(II)chloride (733 mg, 0.9 mmol), sodium carbonate (3.81 g, 35 mmol) and DMF (50 mL) in a 300 mL PARR reactor. Add triethylsilane (11.6 mL, 0.72 mmol) and purge the reactor with carbon monoxide three times. Charge the reactor with carbon monoxide (50 psi); seal; and stir the mixture at 90° C. for 15 hours. Cool the reactor to ambient temperature; filter the resulting mixture over Celite® pad; and wash the pad with DCM (150 mL). Collect the filtrate and sequentially wash the filtrate with water then brine (2×80 mL). Concentrate the organic filtrate under reduced pressure to obtain the residue as an orange oil. Purify by silica gel flash chromatography eluting with hexane/EtOAc (0 to 30% EtOAc) to provide the title compound (5.6 g, 70%, ee>98%). MS (m/z): 228 (M+1).

PREPARATION 8

2-Chloro-3-[[(2S)-oxiran-2-yl]methoxy]pyridine

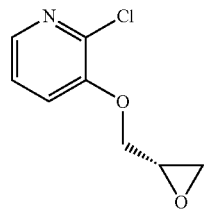 [SMILES: Clc1ncccc1OC[C@@H]1CO1]

Combine (R)-oxiranemethanol (32.85 g, 443.5 mmol) with 2-chloro-3-hydroxypyridine (52.23 g, 403.18 mmol) in THF (1.34 L). Stir the mixture until the solids dissolve. Cool it to 0° C. and slowly add triphenylphosphine (116.33 g, 443.5 mmol). After all the solids dissolve, add diisopropyl azodicarboxylate (87.92 mL, 443.5 mmol) drop-wise over 25 minutes at a sufficiently slow rate to maintain the internal temperature of the reaction below 10° C. Stir the mixture while cooling for 30 minutes then allow the mixture to warm to ambient temperature and continue stirring overnight. Add EtOAc, and wash with NaOH (2×1.0 N). Dry the organic layer over $Na_2SO_4$; filter; and concentrate the filtrate under reduced pressure. Triturate the residue with a mixture of 2:1 $Et_2O$: hexanes and stir for 5 minutes. Filter and concentrate the filtrate under reduced pressure to provide a residue. Purify the residue via flash column chromatography (2×330 g $SiO_2$), eluting with a gradient of 0-66% THF/Hexane. Combine the desired fractions, and concentrate under reduced pressure to provide the title compound (32.6 g, 43.6%) as a white solid. MS (m/z): 186 (M+1).

PREPARATION 9

(2S)-1-Azido-3-[(2-chloro-3-pyridyl)oxy]propan-2-ol

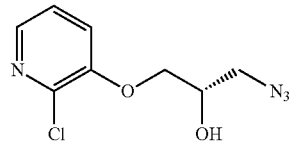 [SMILES: [N-]=[N+]=NC[C@H](O)COc1cccnc1Cl]

Dissolve sodium azide (22.84 g, 351.3 mmol) in water (195 mL). Separately, dissolve 2-chloro-3-[[(2S)-oxiran-2-yl]methoxy]pyridine (32.6 g, 175.6 mmol) in 1,4-dioxane (800 mL). Slowly add the water/sodium azide solution to the dioxane solution; heat to 90° C.; and stir for 1 hour. Cool the mixture and concentrate it under reduced pressure. Add water; extract with EtOAc (2×); combine the extracts; dry the combined extracts over Na$_2$SO$_4$; filter; and collect the filtrate. Remove the solvents under reduced pressure to provide the title compound (40.28 g, 92.8%) as a reddish white solid. MS (m/z): 229 (M+1).

PREPARATION 10

(3S)-3-(Azidomethyl)-2,3-dihydro-[1,4]dioxino[2,3-b]pyridine

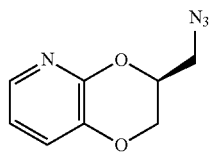 [SMILES: [N-]=[N+]=NC[C@H]1COc2cccnc2O1]

Dissolve (2S)-1-azido-3-[(2-chloro-3-pyridyl)oxy]propan-2-ol (40.28 g, 176.17 mmol) in THF (880 mL) and slowly add sodium hydride (60% dispersion in mineral oil; 14.09 g, 352.35 mmol). Heat the mixture to 90° C. and stir for 2 hours at that temperature. Slowly pour the mixture into 1 liter of packed ice to quench the reaction. Remove the dioxanes under reduced pressure and extract the resulting mixture with EtOAc (3×). Dry the combined extracts over Na$_2$SO$_4$; filter; and concentrate the filtrate under reduced pressure. Purify via flash column chromatography using 2×330 g silica gel, eluting with a gradient of 0-75% of Et$_2$O in hexanes. Combine the product fractions and remove solvents under reduced pressure to provide the title compound as a yellow solid (7.5 g., 22.15%). MS (m/z): 193 (M+1).

PREPARATION 11

[(3S)-2,3-Dihydro-[1,4]dioxino[2,3-b]pyridin-3-yl]methanamine

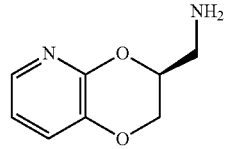 [SMILES: NC[C@H]1COc2cccnc2O1]

Dissolve (3S)-3-(azidomethyl)-2,3-dihydro-[1,4]dioxino[2,3-b]pyridine (7.5 g, 39.03 mmol) in MeOH (390 mL). Degas the mixture by subjecting it to reduced pressure then back filling with nitrogen (3×); add 10% Pd/C (2.08 g, 1.95 mmol); and again degas the mixture. Stir the resulting degassed mixture at ambient temperature under a hydrogen atmosphere for 17 hours. Filter the resulting mixture through Celite® and remove solvents of the filtrate under reduced pressure to provide the title compound (6.5 g, 100%) as an oil. MS (m/z): 167 (M+1).

PREPARATION 12

3,4-Dihydro-2H-1,4-benzoxazine-2-carbonitrile

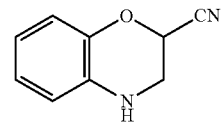 [SMILES: N#CC1CNc2ccccc2O1]

Combine 2-chloro-2-propenenitrile (3.0 g, 34.3 mmol), 2-aminophenol (3.27 g, 29.96 mmol), acetone (50 mL), and potassium chloride (5 g, 36.18 mmol). Stir the mixture at ambient temperature for 16 hours. Filter the mixture and wash the filter cake with EtOAc. Concentrate the filtrate under reduced pressure to give a residue. Purify via flash column chromatography using a gradient of 1-50% EtOAc in petroleum ether to elute. Combine the product fractions and remove solvents under reduced pressure to provide the title compound (1.5 g, 21.6%). MS (m/z): 161 (M+1).

PREPARATION 13

3,4-Dihydro-2H-1,4-benzoxazin-2-ylmethanamine

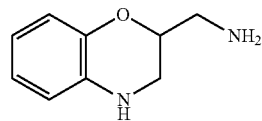 [SMILES: NCC1CNc2ccccc2O1]

Add 3,4-dihydro-2H-1,4-benzoxazine-2-carbonitrile (600 mg, 3.75 mmol) to THF (20 mL) and then slowly add lithium aluminum hydride (1.0 M in THF; 1 mL, 1.0 mmol). Stir the mixture at ambient temperature for 30 minutes. Add H$_2$O (1 mL) to quench the reaction; filter; and wash the filter cake with EtOAc. Dry the filtrate over Na$_2$SO$_4$; filter; and concentrate the filtrate under reduced pressure to afford a residue. Purify the resulting compound via flash column chromatography using a gradient of 20-50% of MeOH in DCM. Combine the desired fractions and remove the solvents under reduced pressure to provide the title compound as a white solid (390 mg, 63.1%). MS (m/z): 165 (M+1).

PREPARATION 14

4-(2,2-Diethoxyethyl)-1,4-benzoxazin-3-one

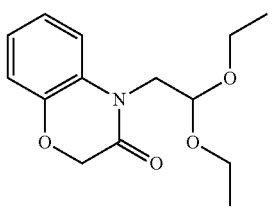 [SMILES: CCOC(CN1C(=O)COc2ccccc21)OCC]

Dissolve 2H-1,4-benzoxazin-3(4H)-one (1.0 g, 6.64 mmol) in dimethylacetamide (5 mL); add potassium tert-butoxide (1.54 g, 13.28 mmol); and stir at ambient temperature for 5 minutes. Add 2-bromo-1,1-diethoxyethane (10.1 mL, 66.4 mmol) and tetra-N-butylammonium iodide (2.49 g, 6.64 mmol). Heat the reaction mixture to 80° C. and stir for 2 hours. Thereafter allow the reaction to cool to ambient temperature. Dilute the reaction mixture with Et$_2$O and water; separate the layers; and extract the aqueous layer with additional Et$_2$O. Combine the organic extracts; dry over Na$_2$SO$_4$; filter; and concentrate the filtrate under reduced pressure. Purify via flash column chromatography using a step gradient of 0%, 10%, 20% and 30% of EtOAc in hexanes. Concentrate the desired fractions to afford the title compound (1.65 g, 93.7%) as a waxy solid. $^1$H (300 MHz, CDCl$_3$): δ 7.36-7.32 (m, 1H), 7.03-6.97 (m, 3H), 4.78 (t, J=5.5 Hz, 1H), 4.59 (s, 2H), 4.02 (d, J=5.5 Hz, 2H), 3.81-3.70 (m, 2H), 3.58-3.48 (m, 2H), 1.16 (t, J=7.0 Hz, 6H).

PREPARATION 15

2-(3-oxo-1,4-benzoxazin-4-yl)acetaldehyde

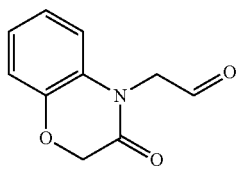 [SMILES: O=CCN1C(=O)COc2ccccc21]

Dissolve 4-(2,2-diethoxyethyl)-1,4-benzoxazin-3-one (710 mg, 2.68 mmol) in THF (5.35 mL) and add aqueous HCl (3 M, 3.57 mL, 10.7 mmol). Stir at ambient temperature for 7 hours. Remove the organic solvent using a stream of nitrogen gas, and extract the aqueous residue with EtOAc. Combine the organic extracts; wash with water and saturated aqueous NaHCO$_3$; and dry over Na$_2$SO$_4$. Filter and remove the solvents from the filtrate under reduced pressure to provide the title compound as a white solid (490 mg, 89.07%). MS (m/z): 192 (M+1).

PREPARATION 16

4-(2-Aminoethyl)-1,4-benzooxazin-3-one

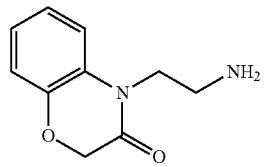 [SMILES: NCCN1C(=O)COc2ccccc21]

Dissolve ammonium acetate (1.3 g, 16.19 mmol) in EtOH (15.69 mL); add 2-(3-oxo-1,4-benzoxazin-4-yl)acetaldehyde (150 mg, 0.78 mmol), sodium cyanoborohydride (155.7 mg, 2.35 mmol), and aqueous ammonia (32%; 5.64 g, 105.91 mmol). Charge a sealable tube with the mixture and seal the tube. Heat to 80° C. and stir overnight. Thereafter allow the mixture to cool to ambient temperature and remove the solvent under reduced pressure. Add EtOAc; wash with brine; NaHCO$_3$ (saturated, aqueous); dry; filter; and concentrate the filtrate under reduced pressure. Purify via flash column chromatography eluting with a step gradient of 5%, 10% and 20% MeOH in DCM. Combine the desired fractions and remove the solvent under reduced pressure to provide the title compound (170 mg, 80%). MS (m/z): 193 (M+1).

PREPARATION 17

Methyl 3-(1-oxo-3,4-dihydroisoquinolin-2(1H)-yl)propanoate

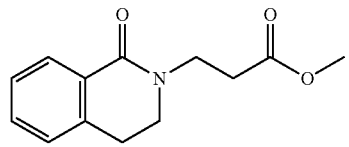 [SMILES: COC(=O)CCN1CCc2ccccc2C1=O]

Dissolve 3,4-dihydroisoquinolin-1(2H)-one (500 mg, 3.40 mmol) in THF (20 mL) and add sodium hydroxide (274.5 mg, 6.79 mmol) followed by methyl acrylate (438.7 mg, 5.10 mmol) in THF (1 mL). Stir the mixture at ambient temperature for 3 hours; quench with water (20 mL); and then dilute with EtOAc (100 mL). Wash the resulting mixture with brine; dry the organic phase over Na$_2$SO$_4$; filter; and concentrate the filtrate under reduced pressure to provide the title compound as a yellow oil (530 mg, 66.9%). MS (m/z): 234 (M+1).

PREPARATION 18

3-(1-Oxo-3,4-dihydroisoquinolin-2(1H)-yl)propanoic acid

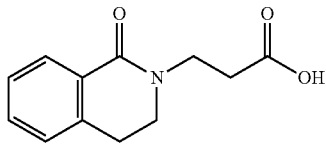 [SMILES: O=C(O)CCN1CCc2ccccc2C1=O]

Dissolve methyl 3-(1-oxo-3,4-dihydroisoquinolin-2(1H)-yl)propanoate (0.3 g, 1.29 mmol) in THF (12 mL) and MeOH (4 mL). Add lithium hydroxide (0.2 g, 8.23 mmol, in 4 mL $H_2O$). Stir at ambient temperature for 2 hours. Evaporate the solvents from reaction mixture under reduced pressure. Adjust the pH to 5 with 2N HCl. Add EtOAc (60 mL); wash with brine; dry over $Na_2SO_4$; filter; and concentrate the filtrate under reduced pressure to provide the title compound (colorless oil, 0.27 g, 95.8%). MS (m/z): 220 (M+1).

PREPARATION 19 tert-Butyl 2-(1-oxo-3,4-dihydroisoquinolin-2(1H)-yl)ethyl carbamate

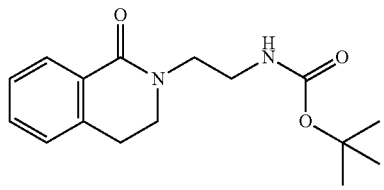 [SMILES: CC(C)(C)OC(=O)NCCN1CCc2ccccc2C1=O]

Combine 3-(1-oxo-3,4-dihydroisoquinolin-2(1H)-yl)propanoic acid (150 mg, 0.53 mmol), diphenylphosphonic azide (489.55 mg, 1.78 mmol), t-butyl alcohol (10 mL), and triethylamine (207.7 mg, 2.05 mmol). Heat the mixture to reflux and stir overnight. Concentrate under reduced pressure and purify the residue via prep-TLC using 10% MeOH/DCM eluting the title compound as a colorless oil (270 mg, 68.0%). MS (m/z): 235 (M-tBu+1).

PREPARATION 20

(1-Oxo-3,4-dihydro-2H-isoquinolin-3-yl)methyl methanesulfonate

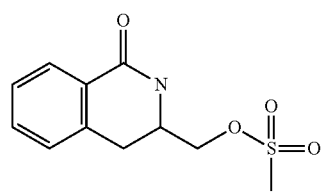 [SMILES: CS(=O)(=O)OCC1Cc2ccccc2C(=O)N1]

Dissolve 3-(hydroxymethyl)-3,4-dihydro-2H-isoquinolin-1-one (6.0 g, 33.86 mmol) in DCM (60 mL) and add triethylamine (7.25 g, 67.72 mmol). Cool to 0° C. and add methanesulfonyl chloride (4.65 g, 40.63 mmol) drop-wise. Stir for one hour; dilute with DCM; and wash with water and then brine. Remove the solvents under reduced pressure to give the title compound (8.0 g, 92%). MS (m/z): 256 (M+1).

PREPARATION 21

3-(Azidomethyl)-3,4-dihydro-2H-isoquinolin-1-one

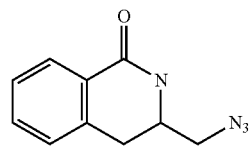 [SMILES: [N-]=[N+]=NCC1Cc2ccccc2C(=O)N1]

Dissolve (1-oxo-3,4-dihydro-2H-isoquinolin-3-yl)methyl methanesulfonate (3 g, 11.7 mmol) in DMF (10 mL). Add $NaN_3$; heat to 70° C. and stir overnight. Concentrate under reduced pressure; add water; and extract with EtOAc. Combine the extracts and remove the solvents under reduced pressure to provide the title compound (1.7 g, 71.5%). $^1H$ NMR (400 mHz, $CDCl_3$): δ 8.1 (s, 1H), 7.6 (m, 1H), 7.5 (m, 1H), 7.0 (s, 1H), 3.9 (m, 1H), 3.5 (m, 2H), 3.0 (m, 2H).

PREPARATION 22

3-(Aminomethyl)-3,4-dihydro-2H-isoquinolin-1-one

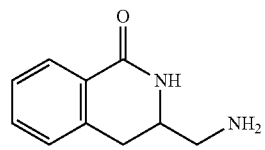 [SMILES: NCC1Cc2ccccc2C(=O)N1]

Dissolve 3-(azidomethyl)-3,4-dihydro-2H-isoquinolin-1-one (1.8 g, 8.9 mmol) in EtOAc (15 mL). Under a nitrogen atmosphere add 10% Pd/C (0.2 g) then stir overnight under a hydrogen atmosphere. Filter reaction mixture through Celite® and wash the Celite® with EtOAc. MS (m/z): 177 (M+1).

PREPARATION 23

3-(Aminomethyl)-3,4-dihydro-2H-isoquinolin-1-one, Isomer 1

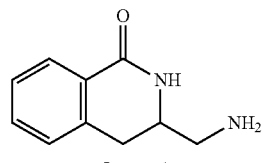

Isomer 1

Separate the enantiomers of 3-(aminomethyl)-3,4-dihydro-2H-isoquinolin-1-one (360 mg, 1.70 mmol) using chiral chromatography conditions L (see below) and collect the first eluting isomer to provide the title compound (140 mg, 47%) MS (m/z): 177 (M+1).

PREPARATION 24 tert-Butyl N-[2-(2-oxo-1,3-benzoxazol-3-yl)ethyl]carbamate

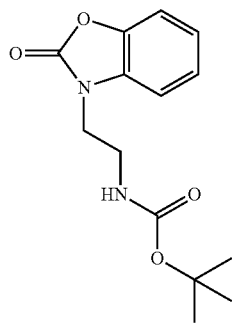 [SMILES: CC(C)(C)OC(=O)NCCn1c(=O)oc2ccccc21]

Combine 2-(3H)-benzoxazolone (0.4 g, 2.9 mmol), tert-butyl 2-bromoethylcarbamate (715.14 mg, 3.19 mmol), potassium tert-butoxide (508.7 mg, 4.35 mmol), potassium iodide (0.1 g, 0.6 mmol) in DMF (6 mL). Heat to 80° C. and stir the mixture overnight. Filter; collect the filtrate; and purify via HPLC conditions M (See below) to provide the title compound (0.53 g, 65.6%) as an oily solid. MS (m/z): 223 (M-tBu+1).

PREPARATION 25

1-Cyclopropyl-2-((2,2-dimethyl-1,3-dioxolan-4-yl)methoxy)ethanone

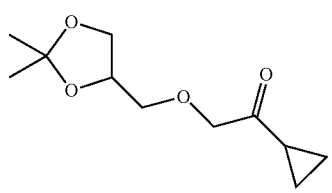

Charge a flask with (2,2-dimethyl-1,3-dioxolan-4-yl)methanol (10 g, 75.7 mmol), heat to 85° C. and add freshly cut sodium (465 mg, 20.23 mmol) Heat to 85° C. and stir for 1 hour. Add 2-bromo-1-cyclopropylethanone (3.0 g, 18.4 mmol) maintain the temperature at 85° C. and stir for 30 minutes. Filter and wash the solid with ACN (20 mL). Collect the filtrate and concentrate under reduced pressure. Purify via HPLC conditions Z to give the title compound as a colorless oil. (650 mg, 16.5%). MS (m/z): 215 (M+1).

PREPARATION 26

1-Cyclopropyl-2-((2,2-dimethyl-1,3-dioxolan-4-yl)methoxy)ethanol

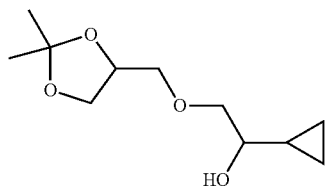

Dissolve 1-cyclopropyl-2-((2,2-dimethyl-1,3-dioxolan-4-yl)methoxy)ethanone (1.2 g, 5.6 mmol), MeOH (20 mL) and sodium tetrahydroborate (310 mg, 8.19 mmol). Stir at ambient temperature for 1 hour. Concentrate under reduced pressure. Add water (30 mL) and extract with EtOAc (3×). Combine the extracts; wash with brine; and dry over MgSO$_4$. Filter; collect the filtrate; and remove the solvents under reduced pressure to give the title compound as a colorless oil (1.2 g, 99%). MS (m/z): 199 (M-H$_2$O+1).

PREPARATION 27

3-(2-Cyclopropyl-2-hydroxyethoxy)propane-1,2-diol

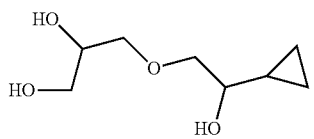 [SMILES: OCC(O)COCC(O)C1CC1]

Dissolve 1-cyclopropyl-2-((2,2-dimethyl-1,3-dioxolan-4-yl)methoxy)ethanol (1.1 g, 5.09 mmol) in MeOH (20 mL) and add HCl (1 M in Et$_2$O; 18 mL, 18 mmol). Stir at ambient temperature for 3 hours. Concentrate under reduced pressure to provide the title product (880 mg, 98.2%) as a colorless oil. MS (m/z): 199 (M+23).

PREPARATION 28

2-(Allyloxy)-2-phenylacetate

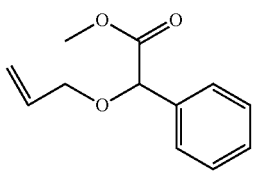

Dissolve methyl 2-hydroxy-2-phenylacetate (1.5 g, 9.03 mmol) and 3-bromoprop-1-ene (1.6 g, 13.23 mmol) in THF (15 mL). Add silver oxide (4.15 g, 17.91 mmol) and heat to 80° C. with microwave irradiation for 2 hours. Filter the material; rinse the solid with THF (30 mL); and concentrate the filtrate under reduced pressure. Purify via flash chromatography using a solution of DCM and petroleum ether (1:1) to provide the title compound as a colorless oil (600 mg, 32.2%). MS (m/z): 207 (M+1).

PREPARATION 29

2-(Allyloxy)-2-phenylacetate

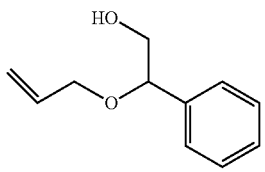

Dissolve 2-(allyloxy)-2-phenylacetate (1.2 g, 5.82 mmol) in THF (40 mL) and add lithium aluminum hydride (1M in THF; 6.40 ml, 6.4 mmol) via syringe. Stir for 2 hours; add ice water (650 mg) to quench the reaction; and stir for another 20 minutes. Filter and wash the solid with THF (20 ml). Concentrate the filtrate under reduced pressure to afford the title compound as a colorless oil (850 mg, 81.97%). MS (m/z): 195 (M+18).

PREPARATION 30

2-(Oxirane-2-ylmethoxy)-2-phenylethanol

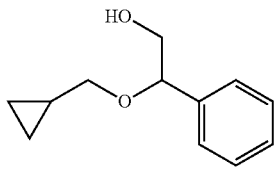 [SMILES: OCC(OCC1CC1)c1ccccc1]

Dissolve 2-(allyloxy)-2-phenylacetate (850 mg, 4.77 mmol) in DCM (40 mL) and add m-chloroperoxybenzoic acid (1.5 g, 8.69 mmol) in a single portion. Stir at ambient temperature overnight. Concentrate under reduced pressure and purify via flash column chromatography using 10% MeOH in DCM to elute. Remove the solvents under reduced pressure to give the product as a colorless oil (900 mg, 97.2%). MS (m/z): 195 (M+1).

PREPARATION 31

2-(Oxirane-2-ylmethoxy)-1-phenylethanol

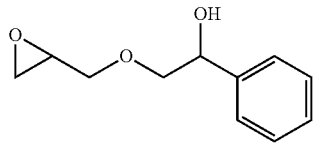 [SMILES: OC(COCC1CO1)c1ccccc1]

Prepare 2-(oxirane-2-ylmethoxy)-1-phenylethanol essentially by the method of Preparation 30. MS (m/z 212 (M+18).

PREPARATION 32 trans-(5-Phenyl-1,4-dioxan-2-yl)methanol

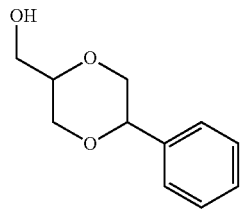 [SMILES: OCC1COC(c2ccccc2)CO1]

Dissolve trans-2-(oxirane-2-ylmethoxy)-2-phenylethanol (800 mg, 4.12 mmol) in 20 mL DCM and add (1S)-(+)-10-camphorsulfonic acid (95 mg, 0.409 mmol). Heat the mixture to reflux and stir overnight. Concentrate under reduced pressure and purify via chromatography conditions R (see below) to provide the title compound (330 mg, 41.25%). $^1$H NMR (300 MHz, CDCl$_3$) δ 7.32 (m, 5H), 4.55 (m, 1H), 3.96 (m, 2H), 3.79-3.52 (m, 5H).

The following compounds in Table 1 are prepared essentially by the method of Preparation 32.

TABLE 1

| Prep. | Chemical name | Structure | MS (m/z): |
|---|---|---|---|
| 33 | (6-Phenyl-1,4-dioxan-2-yl)methanol | 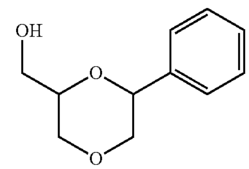 [SMILES: OCC1COCC(c2ccccc2)O1] | 195 (M + 1) |
| 34 | (6-Cyclopropyl-1,4-dioxane-2-yl)methanol | 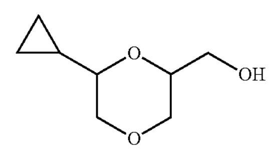 [SMILES: OCC1COCC(C2CC2)O1] | 159 (M + 1) |

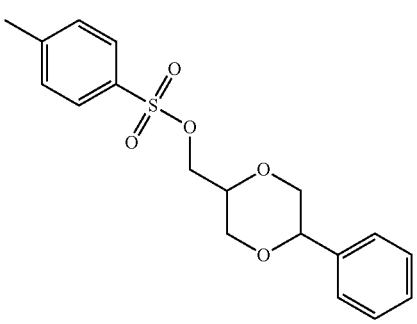 [SMILES: Cc1ccc(S(=O)(=O)OCC2COC(c3ccccc3)CO2)cc1]

PREPARATION 35 trans 5-Phenyl-1,4-dioxan-2-yl)methylbenzenesulfonate

Combine trans-5-phenyl-1,4-dioxan-2-yl)methanol (311 mg, 1.6 mmol), p-toluenesulfonyl chloride (336 mg, 1.76 mmol), N,N-dimethylpyridinamine (195 mg, 1.57 mmol), triethylamine (0.35 mL, 2.51 mmol) and DCM (20 mL). Stir the reaction at ambient temperature overnight. Concentrate under reduced pressure to provide a residue. Purify via flash column chromatography eluting with DCM. Combine the desired fractions, and remove the solvents under reduced pressure to provide the title compound (510 mg, 91.4%) as a white solid. MS (m/z): 349 (M+1)

The following compounds in Table 2 are prepared essentially by the method of Preparation 35.

TABLE 2

| Prep | Chemical name | Structure | MS (m/z): | Chrom Cond. |
|---|---|---|---|---|
| 36 | 6-Phenyl-1,4-dioxan-2-yl)methyl-4-methylbenzene-sulfonate | 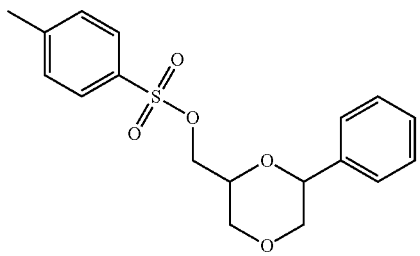 [SMILES: Cc1ccc(S(=O)(=O)OCC2COCC(c3ccccc3)O2)cc1] | 366 (M + 18) | |
| 37 | cis-6-Cyclopropyl-1,4-dioxan-2-yl)methyl-4-methylbenzene-sulfonate | 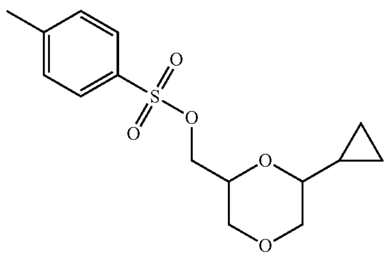 [SMILES: Cc1ccc(S(=O)(=O)OCC2COCC(C3CC3)O2)cc1] | 313 (M + 1) | W |

PREPARATION 38 trans-2-Azidomethyl-5-phenyl-1,4-dioxane

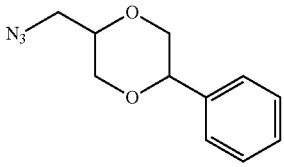 [SMILES: [N-]=[N+]=NCC1COC(c2ccccc2)CO1]

Dissolve trans-5-phenyl-1,4-dioxan-2-yl)methylbenzene-sulfonate (510 mg, 1.46 mmol) in DMF (10 mL). Add sodium azide (152 mg, 2.34 mmol) to the DMF solution in a single portion. Heat the mixture to 105° C. and stir for 2 hours. Quench with $H_2O$ (20 mL), and extract with EtOAc (3×20 mL). Wash the organic extracts with brine; dry over $MgSO_4$; filter; and concentrate the filtrate to provide the title compound as a colorless oil. (319 mg, 99.4%). MS (m/z): 242 (M+23).

The following compounds in Table 3 are prepared essentially by the method of Preparation 38.

TABLE 3

| Prep | Chemical name | Structure | MS (m/z): |
|---|---|---|---|
| 39 | 2-(Azidomethyl)-6-phenyl-1,4-dioxane | 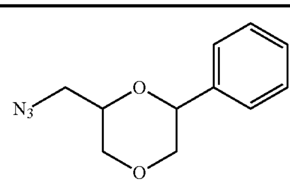 | 237 (M + 18) |

TABLE 3-continued

| Prep | Chemical name | Structure | MS (m/z): |
|---|---|---|---|
| 40 | cis-2-(Azidomethyl)-6-cyclopropyl-1,4-dioxane | 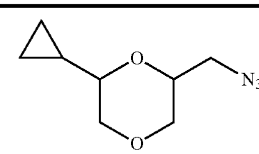 | 183 (M + 1) |

PREPARATION 41

(trans-5-Phenyl-1,4-dioxan-2-yl)methanamine

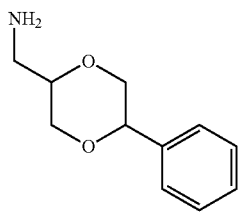

Combine trans-2-azidomethyl-5-phenyl-1,4-dioxane (319 mg, 1.46 mmol), triphenylphosphine (765 mg, 2.92 mmol), and THF (20 mL) and $H_2O$ (5 mL). Stir the reaction mixture at room temperature overnight. Add Dowex AG 50W-X8 cation exchange resin (ammonium form, 200-400 mesh, 1 g) to the reaction and stir at ambient temperature for 20 minutes. Filter and sequentially wash the resin with THF (10 mL) then $H_2O$ (10 mL). Elute by rinsing the SCX resin with $NH_3$ in MeOH (120 mL 7N) and concentrate the filtrate under reduced pressure to provide the title compound (280 mg, 99.6%) as a colorless oil. MS (m/z): 194 (M+1).

The following compounds in Table 4 are prepared essentially by the method of Preparation 41.

TABLE 4

| Prep | Chemical name | Structure | MS (m/z) | Chrom Cond. |
|---|---|---|---|---|
| 42 | trans (6-Phenyl-1,4-dioxan-2-yl)methanamine | 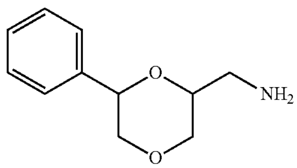 [SMILES: NCC1COCC(c2ccccc2)O1] | 194 (M + 1) | Q |
| 43 | cis (6-Phenyl-1,4-dioxan-2-yl)methanamine | 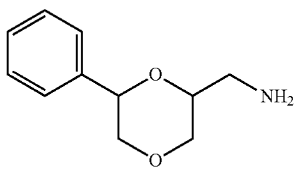 [SMILES: NCC1COCC(c2ccccc2)O1] | 194 (M + 1) | Q |
| 44 | ((cis)-6-Cyclopropyl-1,4-dixoan-2-yl)methanamine | 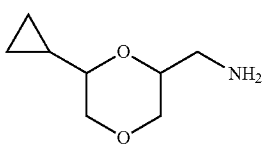 [SMILES: NCC1COCC(C2CC2)O1] | 158 (M + 1) | |

EXAMPLE 1

N-{(1S)-1-[4-({[(3S)-2,3-Dihydro[1,4]dioxino[2,3-b]pyridin-3-ylmethyl]amino}methyl)phenyl]-2,2,2-trifluoroethyl}methanesulfonamide hydrochloride

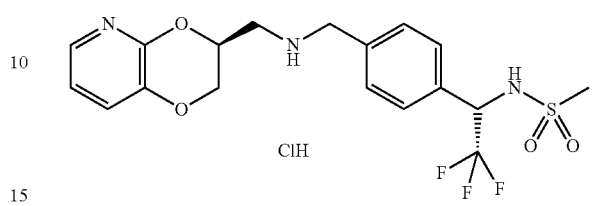

Combine [(3S)-2,3-dihydro-[1,4]dioxino[2,3-b]pyridin-3-YL]methanamine (9.71 g, 58.4 mmol), N-[(1S)-2,2,2-trifluoro-1-(4-formylphenyl)-ethyl]-methanesulfonamide (16.43 g, 58.4 mmol) and MeOH (292 mL). Add 4 Å Molecular Sieves (30 mL) and stir the mixture at ambient temperature under a nitrogen atmosphere for 1 h. Add sodium borohydride (8.84 g, 233.7 mmol) portionwise and stir at ambient temperature for 10 minutes, monitoring the reaction via MS and $^1$H NMR. Slowly add H$_2$O to quench the reaction and filter through Celite®. Collect the filtrate; remove solvents under reduced pressure; and purify via flash column chromatography using a gradient of 0-100% of (5% (2N NH$_3$/MeOH) in DCM) in (5% MeOH/DCM) to elute the product. Combine the product fractions, and remove solvents under reduced pressure to afford the free base as a residue. Dissolve the residue in DCM, and add HCl (1N in Et$_2$O; 87.7 mL, 87.7 mmol) while stirring. Stir for 10 minutes after the addition is complete, then remove the solvents under reduced pressure to provide the title product (12.9 g, 47.3%) as a white solid. MS (m/z): 432 (M-Cl).

The following Examples in Table 5 can be prepared essentially by the method of Example 1. All the following Examples in Table 5 were isolated as single isomers either by starting from chiral starting materials and/or using the chromatographic columns and conditions identified below.

TABLE 5

| Ex # | Chemical name | Structure | MS (m/z) | Chrom Cond. |
|---|---|---|---|---|
| 2 | N-{(1R)-1-[4-({[(3S)-2,3-Dihydro[1,4]dioxino[2,3-b]pyridin-3-ylmethyl]amino}methyl)phenyl]ethyl}methanesulfonamide hydrochloride | 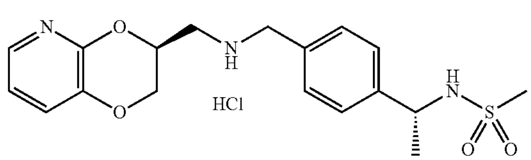 [SMILES: C[C@@H](NS(C)(=O)=O)c1ccc(CNC[C@H]2COc3cccnc3O2)cc1 ; Cl] | 378 (M – Cl) | |
| 3 | N-((1R)-1-[4-({[(7-Fluoro-2,3-dihydro-1,4-benzodioxin-2-yl)methyl]amino}methyl)phenyl]ethyl}methanesulfonamide hydrochloride, Isomer 1 | Isomer 1 | 395 (M – Cl) | D |

TABLE 5-continued

| Ex # | Chemical name | MS (m/z) | Chrom Cond. |
|---|---|---|---|
| 4 | N-{(1R)-1-[4-({[(2R)-2,3-Dihydro-1,4-benzodioxin-2-ylmethyl]amino}methyl)phenyl]ethyl}methanesulfonamide hydrochloride | 377 (M − Cl) | |
| 5 | N-{(1R)-1-[4-({[(2S)-2,3-Dihydro-1,4-benzodioxin-2-ylmethyl]amino}methyl)phenyl]ethyl}methanesulfonamide hydrochloride | 377 (M − Cl) | |
| 6 | N-[(1R)-1-(4-{[(3,4-Dihydro-1H-isochromen-3-ylmethyl)amino]methyl}phenyl)ethyl]methanesulfonamide hydrochloride, Isomer 1 | 375 (M − Cl) | F |
| 7 | N-[(1R)-1-(4-{[(3,4-Dihydro-1H-isochromen-3-ylmethyl)amino]methyl}phenyl)ethyl]methanesulfonamide hydrochloride, Isomer 2 | 375 (M − Cl) | F |
| 8 | N-[(1S)-1-(4-{[(3,4-Dihydro-1H-isochromen-3-ylmethyl)amino]methyl}phenyl)-2,2,2-trifluoroethyl]methanesulfonamide hydrochloride, Isomer 2 | 429 (M − Cl) | F |
| 9 | N-[(1R)-1-(4-{[(3,4-Dihydro-2h-pyrano[2,3-b]pyridin-2-ylmethyl)amino]methyl}phenyl)ethyl]methanesulfonamide hydrochloride Isomer 2 | 376 (M − Cl) | G |
| 10 | N-[(1S)-1-(4-{[(2,3-Dihydro-1,4-benzodioxin-2-ylmethyl)amino]methyl}phenyl)-2,2,2-trifluoroethyl]methanesulfonamide hydrochloride, Isomer 1 | 431 (M − Cl) | B |
| 11 | N-[(1S)-1-(4-{[(2,3-Dihydro-1,4-benzodioxin-2-ylmethyl)amino]methyl}phenyl)-2,2,2-trifluoroethyl]methanesulfonamide hydrochloride, Isomer 2 | 431 (M − Cl) | C |

TABLE 5-continued

| Ex # | Chemical name | Structure | MS (m/z) | Chrom Cond. |
|---|---|---|---|---|
| 12 | N-[(1R)-1-(4-{[(2,3-Dihydro-1-benzofuran-2-ylmethyl)amino]methyl}phenyl)ethyl]methane-sulfonamide hydrochloride, Isomer 2 | 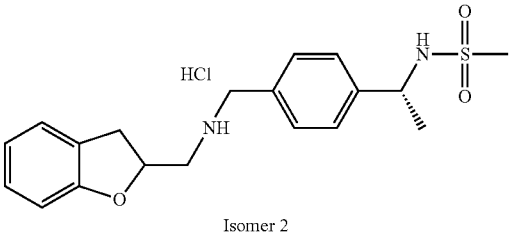 Isomer 2 | 361 (M − Cl) | A |
| 13 | N-[(1R)-1-(4-{[(3,4-Dihydro-2h-1,4-Benzoxazin-3-ylmethyl)Amino]Methyl}Phenyl)Ethyl]Methane-sulfonamide dihydrochloride Isomer 1 | 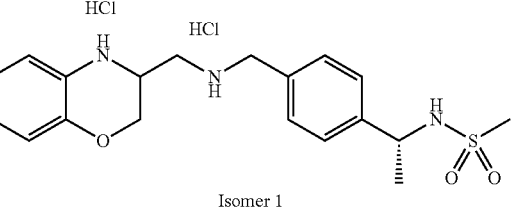 Isomer 1 | 376 (M − 2HCl + 1) | C |
| 14 | N-[(1R)-1-(4-{[(3,4-Dihydro-2h-1,4-benzoxazin-3-ylmethyl)amino]methyl}phenyl)ethyl]methane-sulfonamide dihydrochloride Isomer 2 | 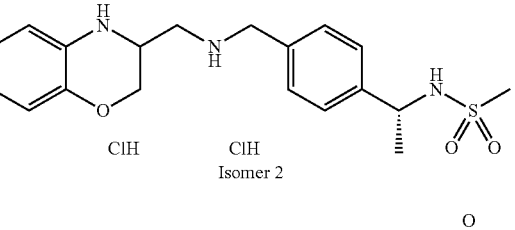 Isomer 2 | 376 (M − 2HCl + 1) | C |
| 15 | N-{(1R)-1-[4-({[(2r)-3,4-dihydro-2h-chromen-2-ylmethyl]amino}methyl)phenyl]ethyl}methane-sulfonamido hydrochloride | 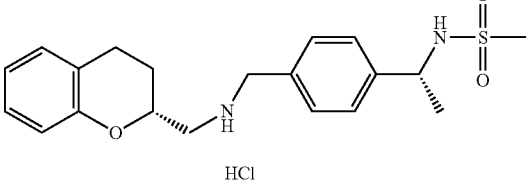 | 375 (M − Cl) | |
| 16 | N-[(1R)-1-(4-{[(3,4-Dihydro-2h-1,4-benzoxazin-2-ylmethyl)amino]methyl}phenyl)ethyl]methane-sulfonamide dihydrochloride Isomer 2 | 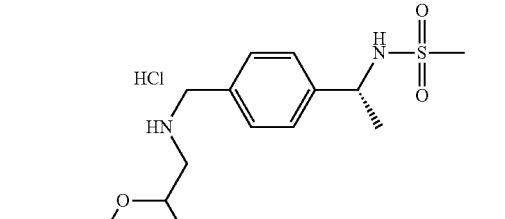 Isomer 2 | 376 (M − 2HCl + 1) | J |
| 17 | N-[(1S)-2,2,2-Trifluoro-1-(4-{[(tetrahydro-2h-pyran-2-ylmethyl)amino]methyl}phenyl)ethyl]methane-sulfonamide hydrochloride, Isomer 1 | 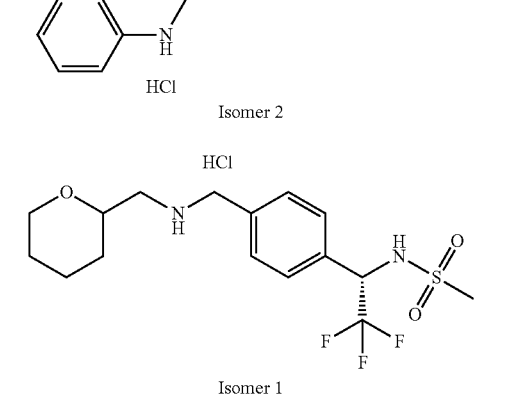 Isomer 1 | 381 (M − Cl) | N |

TABLE 5-continued

| Ex # | Chemical name | Structure | MS (m/z) | Chrom Cond. |
|---|---|---|---|---|
| 18 | N-{(1R)-1-[4-({[(4-Phenylmorpholin-2-yl)methyl]amino}methyl)phenyl]ethyl}methane-sulfonamide hydrochloride, Isomer 2 | 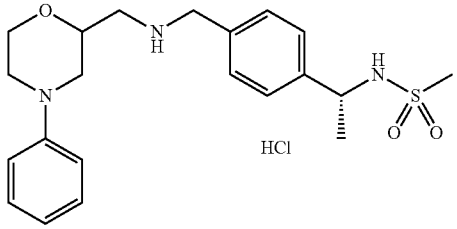 [SMILES: C[C@@H](NS(C)(=O)=O)c1ccc(CNCC2CN(c3ccccc3)CCO2)cc1 ; Cl]<br>Isomer 2 | 404 (M − Cl) | O |
| 19 | N-[(1R)-1-(4-{[(1-Phenylpyrrolidin-3-yl)amino]methyl}phenyl)ethyl]methanesulfonamide dihydrochloride, Isomer 2 | 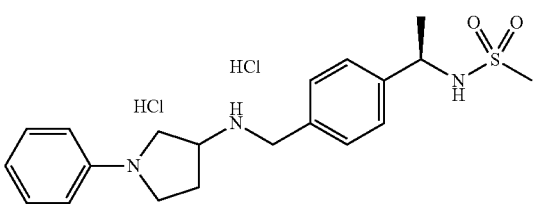 [SMILES: C[C@@H](NS(C)(=O)=O)c1ccc(CNC2CCN(c3ccccc3)C2)cc1 ; Cl ; Cl]<br>Isomer 2 | 374 (M − 2HCl + 1) | P |
| 20 | cis N-[(1R)-1-(4-{[(5-Phenyltetrahydrofuran-3-yl)amino]methyl}phenyl)ethyl]methanesulfonamide hydrochloride, Isomer 1 | 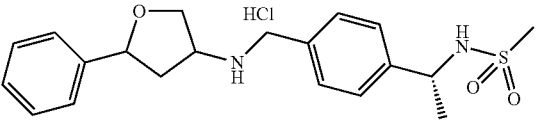 [SMILES: C[C@@H](NS(C)(=O)=O)c1ccc(CNC2COC(c3ccccc3)C2)cc1 ; Cl]<br>Isomer 1 | 375 (M − Cl) | K |
| 21 | cis N-[(1R)-1-(4-{[(5-Phenyltetrahydrofuran-3-yl)amino]methyl}phenyl)ethyl]methanesulfonamide hydrochloride Isomer 2 | 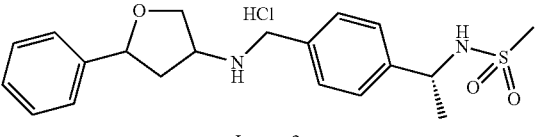<br>Isomer 2 | 375 (M − Cl) | K |
| 22 | N-{(1S)-2,2,2-Trifluoro-1-[4-({[2-(3-oxo-2,3-dihydro-4h-1,4-benzoxazin-4-yl)ethyl]amino}methyl)phenyl]ethyl}methane-sulfonamide hydrochloride | 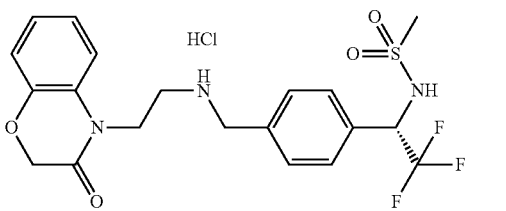 [SMILES: CS(=O)(=O)N[C@@H](c1ccc(CNCCN2C(=O)COc3ccccc32)cc1)C(F)(F)F ; Cl] | 458 (M − Cl) | |
| 23 | N-{(1R)-1-[4-({[(1-Oxo-1,2,3,4-tetrahydroisoquinolin-3-yl)methyl]amino}methyl)phenyl]ethyl}methane-sulfonamide hydrochloride Isomer 1 | 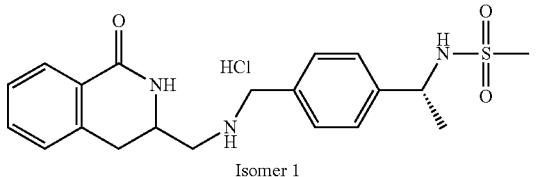<br>Isomer 1 | 388 (M − Cl) | Y |
| 24 | N-{(1S)-2,2,2-Trifluoro-1-[4-({[(1-oxo-1,2,3,4-tetrahydroisoquinolin-3-yl)methyl]amino}methyl)phenyl]ethyl}methane-sulfonamide hydrochloride Isomer 1 | 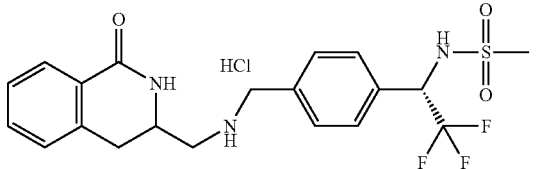 [SMILES: CS(=O)(=O)N[C@@H](c1ccc(CNCC2Cc3ccccc3C(=O)N2)cc1)C(F)(F)F ; Cl]<br>Isomer 1 | 442 (M − Cl) | |

TABLE 5-continued

| Ex # | Chemical name | Structure | MS (m/z) | Chrom Cond. |
|---|---|---|---|---|
| 25 | N-{1-[4-({[(4-Methyl-3,4-dihydro-2h-1,4-benzoxazin-2-yl)methyl]amino}methyl)phenyl]ethyl}methane-sulfonamide dihydrochloride Isomer 1 | 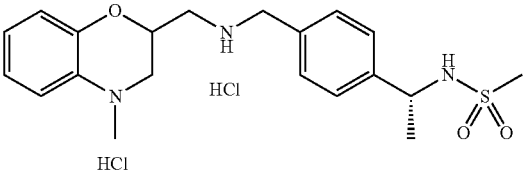 [SMILES: C[C@@H](NS(C)(=O)=O)c1ccc(CNCC2CN(C)c3ccccc3O2)cc1 ; Cl ; Cl] Isomer 1 | 390 (M − 2HCl + 1) | H |
| 26 | N-{1-[4-({[(4-Methyl-3,4-dihydro-2h-1,4-benzoxazin-2-yl)methyl]amino}methyl)phenyl]ethyl}methane-sulfonamide dihydrochloride Isomer 2 | 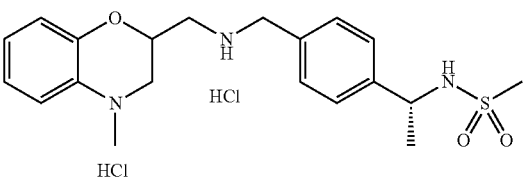 [SMILES: C[C@@H](NS(C)(=O)=O)c1ccc(CNCC2CN(C)c3ccccc3O2)cc1 ; Cl ; Cl] Isomer 2 | 390 (M − 2HCl + 1) | H |
| 27 | trans N-{(1R)-1-[4-({[(6-Phenyl-1,4-dioxan-2-yl)methyl]amino}methyl)phenyl]ethyl}methane-sulfonamide hydrochloride Isomer 1 | 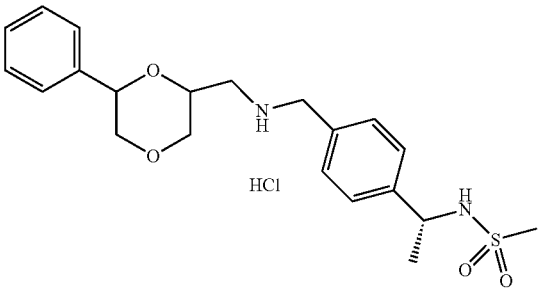 [SMILES: C[C@@H](NS(C)(=O)=O)c1ccc(CNCC2COCC(c3ccccc3)O2)cc1 ; Cl] | 405 (M − Cl) | T |
| 28 | cis N-{(1R)-1-[4-({[(6-Phenyl-1,4-dioxan-2-yl)methyl]amino}methyl)phenyl]ethyl}methane-sulfonamide hydrochloride Isomer 2 | 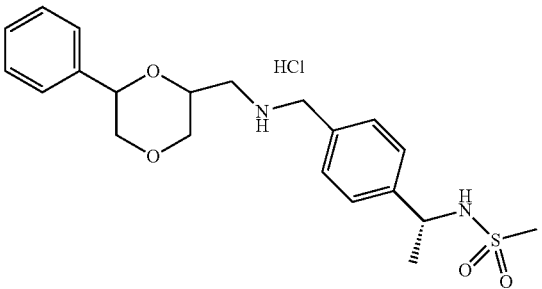 [SMILES: C[C@@H](NS(C)(=O)=O)c1ccc(CNCC2COCC(c3ccccc3)O2)cc1 ; Cl] Isomer 2, Cis | 405 (M − Cl) | T |
| 29 | trans-N-{(1R)-1-[4-({[(5-Phenyl-1,4-dioxan-2-yl)methyl]amino}methyl)phenyl]ethyl}methane-sulfonamide hydrochloride Isomer 2 | 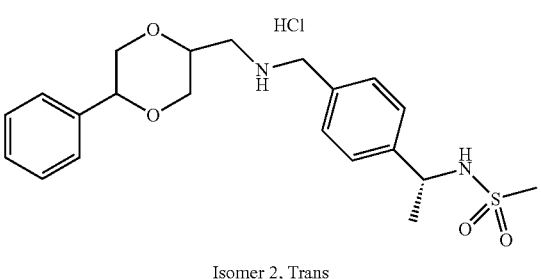 Isomer 2, Trans | 405 (M − Cl) | S |

TABLE 5-continued

| Ex # | Chemical name | Structure | MS (m/z) | Chrom Cond. |
|---|---|---|---|---|
| 30 | cis-N-{(1S)-1-[4-({[(6-Pyclopropyl-1,4-dioxan-2-yl)methyl]amino}methyl)phenyl]-2,2,2-trifluoroethyl}methanesulfonamide hydrochloride Isomer 1 | Isomer 1, Cis | 423 (M – Cl) | U |

EXAMPLE 31

N-{(1S)-2,2,2-Trifluoro-1-[4-({[2-(1-oxo-3,4-dihydroisoquinolin-2(1H)-yl)ethyl]amino}methyl)phenyl]ethyl}methanesulfonamide hydrochloride

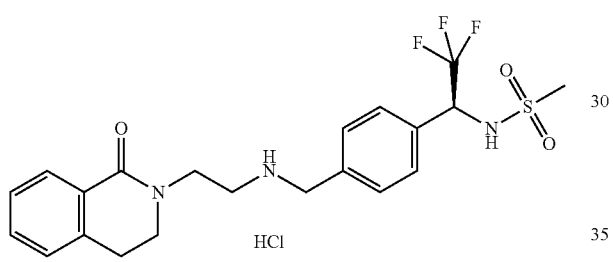

Dissolve tert-butyl 2-(1-oxo-3,4-dihydroisoquinolin-2(1H)-yl)ethylcarbamate (220 mg, 0.76 mmol) in DCM (3 mL) and add trifluoroacetic acid (1 mL, 13.23 mmol). Stir at ambient temperature for 30 minutes. Concentrate the mixture under reduced pressure, then dissolve in 1,2-dichloroethane (20 mL). Add N-[(1S)-2,2,2-trifluoro-1-(4-formylphenyl)-ethyl]-methanesulfonamide (150 mg, 0.53 mmol), acetic acid (0.05 mL, 0.87 mmol), and sodium triacetoxyborohydride (642.3 mg, 3.03 mmol). Stir the mixture at ambient temperature overnight. Concentrate under reduced pressure to give a residue and dilute the residue with MeOH (2 mL). Purify the residue via preparatory TLC using 10% MeOH in DCM to give a colorless oil. Dissolve the oil in MeOH (3 mL) and add HCl (1M in diethyl ether; 0.5 mL, 0.5 mmol) and stir for 30 minutes. Concentrate under reduced pressure to give the title compound as a white solid (10 mg, 3.7%). MS (m/z): 456 (M-Cl).

EXAMPLE 32

N-{(1S)-2,2,2-Trifluoro-1-[4-({[2-(2-oxo-1,3-benzoxazol-3(2h)-yl)ethyl]amino}methyl)phenyl]ethyl}methanesulfonamide hydrochloride Prepare N-{(1S)-2,2,2-trifluoro-1-[4-({[2-(2-oxo-1,3-benzoxazol-3(2h)-yl)ethyl]amino}methyl)phenyl]ethyl}methanesulfonamide hydrochloride essentially by the method of Preparation for Example 31. MS (m/z) 444 (M-Cl).

Table 6 provides the chromatography conditions where they vary from the Examples above.

TABLE 6

| Conditions | Column | Column Size | Mobile Phase |
|---|---|---|---|
| A | Chiralpak AD | 20 × 250 mm 10 um | EtOH 100% |
| B | Chiralpak AD-H | 21 × 150 mm 5 um | $CO_2$/IPA (0.2% IPAm) 80/20 |
| C | Chiralpak IC-H | 30 × 250 5 um | Hexane/EtOH(0.1% DEA) 55/45 |
| D | Chiralpak AD-H | 21 × 150 mm 5 um | $CO_2$/IPA (0.2% IPAm) 70/30 |
| F | Chiralpak AY | 30 × 250 mm 5 um | Hexane/EtOH(0.1% DEA) 30/70 |
| G | Chiralpak AY-H | 30 mm | 30% MeOH(0.1% DEA)/$CO_2$ |
| H | Chiralcel OD-H | 30 × 250 mm 5 um | 40% MeOH(0.1% DEA)/$CO_2$ |
| J | Chiralpak AY-H | 30 × 250 mm 5 um | Hexane/EtOH(0.1% DEA) 60/40 |
| K | Chiralcel OJ-H | 30 × 250 mm 5 um | MeOH(0.2% IPAm) |
| L | Chiralcel OJ | 20 × 250 mm 10 um | Hexane (0.2% DMEA)/IPA 75/25 |
| M | Shimadzu C18 | 19 × 250 mm 15 um | 45-55% (10 mmol $NH_4HCO_3/H_2O$)/acetonitrile. |
| N | Chiralcel OD | 21.2 × 250 mm 10 um | Hexane (0.2% DMEA)/IPA 70/30 |
| O | Chiralpak AD-H | 20 × 250 mm 5 um | $CO_2$/IPA-DEA (0.2%) 70/30 |

TABLE 6-continued

| Conditions | Column | Column Size | Mobile Phase |
|---|---|---|---|
| P | Chiralpak AS | 20 × 250 mm 10 um | Hexane (0.2% DMEA)/ethanol 75/25 |
| Q | Shimadzu PRC-ODS | 20 × 250 mm 15 um | 10-30% (10 mmol $NH_4HCO_3/H_2O$)/acetonitrile. |
| R | Shimadzu C18 | 19 × 250 mm 15 um | 30-40% (10 mmol $NH_4HCO_3/H_2O$)/acetonitrile. |
| S | RegisCell OD | 30 × 250 mm 5 um | $CO_2$/[MeOH-DEA (0.1%) 14-56% Gradient] |
| T | Chiralpak IA | 30 × 250 mm 5 um | Hexane:EtOH(0.1% DEA), 70:30 |
| U | AD | 30 × 250 mm 5 um | $CO_2$/MeOH-DEA (0.1%) 85/15 |
| W | Shimadzu C18 | 19 × 250 mm 15 um | (10 mmol $NH_4HCO_3/H_2O$)/acetonitrile 40/60 |
| X | Chiralpak AD | 20 × 250 mm 10 um | Methanol(0.2% DMEA) 100% |
| Y | Chiralcel OJ | 10 × 250 mm 10 um | (0.2% DMEA in EtOH) 100% |
| Z | Shimadzu PRC-ODS | 20 × 250 mm 15 um | 25-50% ACN/water (10 mMol/L $NH_4HCO_3$) |

MOGAT-2 Inhibitory Assay

The in vitro inhibitory activity of compounds against human MoGAT-2 is evaluated in this assay. MoGAT-2 transfers an oleoyl group to monooleoyl-glycerol ("MAG") from oleoyl-CoA to form dioleoyl-glycerol ("DAG") in the intestinal triglyceride resynthesis pathway. The assay takes advantage of Microscint E extraction, which extracts hydrophobic molecules selectively over hydrophilic ones to separate the $^{14}$C-oleoyl-CoA from $^{14}$C-DAG.

Genetically engineered insect SF9 cells express human MoGAT-2. Prepare the cell lysate in 20 mM of NaCl with protease inhibitor (Roche Cat#11873580001). Homogenize the SF9 cells expressing human MoGAT-2 at 15,000 rpm for 20×2 seconds (PT-3100 Polytrone). Centrifuge the homogenate at 1000 g for 10 minutes at 4° C. Collect the supernatant into a separate tube for protein quantification and activity testing. Purify the glycerol monooleate substrate (Spectrum Chemical, CAS#25496-72-4) chromatographically. Prepare the monoacylglycerol (MAG) substrate in phospholipid vescicles (dioleoyl phosphatidylcholine "DOPC"). Prepare the MAG/DOPC vesicles at 20 mM concentration of total lipids (MAG and DOPC). Prepare different molar ratios of MAG to total lipids for either compound screening (8.9%) or compound kinetic studies (2.6-40%). Mix the appropriate amount of purified MAG and DOPC (Avanti Polar Lipids #850375C) in chloroform in a glass tube. Subsequently, evaporate chloroform under stream of $N_2$ gas and then dry under reduced pressure for 30 minutes. Add an appropriate amount of buffer (Tris-Cl pH 7.4, 250 mM sucrose, 1 mM EDTA) to the dried MAG/DOPC mixture for the desired total lipid concentration. Sonicate the MAG/DOPC solution until the solution is clear. Measure the vesicle size using dynamic light scattering to confirm uniformity.

The assay buffer consists of 100 mM Tris, pH 7.5 (Invitrogen 15567-022), 11% DMSO, 250 mM sucrose (Sigma S-0389), 1 mM, EDTA, and Complete Protease Inhibitor cocktail (Roche Diagnostic 12454800). Add the test compounds to the buffer together with the substrates and enzymes. The final concentration for the reaction is 0.016 mg/mL SF9 cell extract, 20 μM oleoyl-CoA (3.5 μM $^{14}$C-oleoyl-CoA), 1.26 mM total lipid in the form of sonicated vesicles, composed of 8.9:91.1 (molar ratio) MAG:DOPC. Stop the reaction after 90 minutes of incubation at room temperature by adding AESSM (12.5% of 100% denatured EtOH; 11% DI H2O; 2.5% 1.0N NaOH; 59% Isopropanol (Mallinckrodt 3031-08); 15% Heptane (Omni Solv HX0078)), by volume. Add Microscint E and then seal the plates and count on a scintillation counter after at least 4 hours of equilibration at room temperature. Calculate the $IC_{50}$ (concentration to reach half maximum inhibition) using Excel Fit software (version 4; Data analyzing using a 4-parameter non-linear logistic equation (ABase Equation 205)) by plotting concentration vs relative MoGAT-2 activity.

All the compounds exemplified herein have an $IC_{50}$ of less than 100 nM. Example 1 exhibits an $IC_{50}$ of 2.28 nM. The results demonstrate that the exemplified compounds are inhibitors of the MoGAT-2 this assay.

Inhibitory Activity in MOGAT-2 Cell Assay

The inhibitory activity of compounds against human MoGAT-2 in a cell environment is evaluated in this assay. Caco-2 is a human colon carcinoma cell line and is often used as a model for intestinal epithelial cells. Caco-2 does not express MoGAT-2, and, thus, human MoGAT-2 is engineered into the cell line through a stable transfection. A MAG analogue, 2-O-Hexadecylglycerol (HDG), is utilized to detect cellular MoGAT-2 activity, because HDG is not hydrolyzed and the resulting product is readily monitored by mass spectrometry. The substrate is delivered to cells using as a mixture with DOPC in the form of sonicated vesicles.

Seed the Caco2 cells onto 100 mm dishes to be 80% confluent after 24 hours in complete media (3/1 DMEM: F12+ 10% FBS+20 mM HEPES+gentamicin). Transfect the cells with hMoGAT-2 plasmid (MOGAT-2-pCDNA3.1-Hygro) using Lipofectamine 2000 (Invitrogen). After a 6 hour exposure to the transfection mixture, wash the cells three times in PBS and then add media. Incubate the cells for an additional 18 hours incubation, trypsinize the cells and serially dilute them into 100 mm dishes. Add complete media+400 μg/ml hygromycin and incubate until clones appear. Isolate and transfer the clones into 24 well dishes and grow to confluency. Prepare the RNAs from these clones using a Qiagen RNAeasy kit. Perform Taqman analysis using an ABI inventoried assay (HS00228262) on a 7900 Sequence Detection System (ABI). Analyze the lysates from these clones by Western blot analysis using a goat polyclonal antibody (Santa Cruz, SC-32392 to confirm human MoGAT-2 expression of a 38 kD protein corresponding to MoGAT-2.

Mix 2-O-hexadecylglycerol ("HDG", Biosynth Chemistry & Biology, # H-1806, 562.7 μL of 20 mg/ml) and DOPC (14.3 ml of 20 mg/ml) in chloroform in a glass tube; dry first under $N_2$ gas; and then under reduced pressure for additional 30 minutes. Add 20 ml of buffer (150 mM Tris-Cl pH 7.4, 250 mM sucrose, 1 mM EDTA) to the dried HDG/DOPC mixture while sonicating until the solution becomes clear. Plate the Caco2 cells into a poly-D-lysine coated 96-well plate (the "Cell Plate") at 37° C., 5% $CO_2$ overnight. Remove the growth media and pretreat the cells with the test compound in DMEMF12 (3:1) media (GIBCO 93-0152DK) containing 2% BSA (Sigma) for 30 minutes. Treat the cells with one test compound in 2% BSA DMEMF12 (3:1) media containing 40 μM of oleic acid and 800 μM of 8.9:91.9 (molar ratio) HDG/DOPC for 4 hours. Trypsinize the cells with 50 μl of trypsin solution and add 50 μl of PBS. Immediately freeze the cells on dry ice and store at −20° C. for LC-MS analysis. Extract the cells with chloroform/methanol as follows: transfer the cells to a 2 ml plate; wash the cell plate with 200 μL methanol and then transfer the methanol wash to the 2 ml plate; wash the cell plate again with 200 μL PBS and transfer the PBS wash to the 2 ml plate. Add chloroform (400 μL) with an internal standard (19.52 ng/mL) DAG (15:0,15:0 (Sigma)), D5-TAG (39.03 ng/mL) CDN (16,16,16) to the 2 mL Plate. Turn the sealed 2 mL Plate up and down (10×), then vortex and spin. Remove 400 μL of the lower layer from the 2 mL plate and add to the wells of another plate the "Final Plate". Add CHCl$_3$:MeOH (400 μL 2:1) to the 2 mL Plate. Again turn the sealed 2 mL Plate up and down (10×), vortex and spin. Remove 220 μL of the lower layer from the 2 mL Plate and add to the Final Plate. Dry the Final Plate and reconstitute with 500 mL of IPA. Seal the Final Plate and shake for 5 min Inject 10 μl of a sample from the Final Plate onto a Halo C8 column (2.1×50, 2.7 uL particle size) held at 60° C. using a Leap auto sampler with a 10 μL loop, interfaced to a Shimadzu solvent delivery system. Monitor the channels to collect data for the D5 C16 TAG internal standard as well as the ether TAG, and C52 and C54 natural TAGs. Solvent A is 80/20 H$_2$O/Methanol with 20 μM ammonium acetate. Solvent B is 50/50 IPA/THF with 20 μM ammonium acetate. Flow rate is 0.4 mL/min Wash solvents are H$_2$O/MeOH and DCM. Using Xcalibur software extract the areas of the peaks of interest, and export the data to Excel which uses the following formula: (area of ether TAG/area of C54 natural TAG)/Area of IS. This ratio effectively accounts for variance of cell number in each well.

The results for this MOGAT-2 cell based assay are provided below in Table 7 and demonstrate that the Examples listed in Table 7 inhibit the human MoGAT-2 in the cell environment.

TABLE 7

| Example | C$_{50}$ nM (Std Dev.; n*) |
|---|---|
| 1 | 3.8 (2.7; 2) |
| 14 | 479 (N/A; 1) |
| 19 | 105 (N/A; 1) |
| 29 | 294 (N/A; 1) |
| 31 | 266 (N/A; 1) |

*number of experiments

Pharmacological Effects in a Dog Oil Bolus Model

Inhibiting MoGAT-2 found in the small intestine may be useful for treating hypertriglyceridemia caused by excessive fat intake Inhibition of MoGAT-2 disrupts resynthesis of triglycerides, which reduces secretion of triglycerides from the intestine. Therefore, MoGAT-2 inhibition interferes with a specific process that leads to eventual secretion of triglycerides into the intestine for eventual circulation through the body. To assess the ability of one or more of the exemplified compounds to inhibit MoGAT-2 induced TAG secretion into the intestine as measured in the blood system, the following protocol can be followed:

Twenty one male beagles are enrolled for each study, each dog selected to have a body weight between 9-13 kg. House the dogs in cages with a standard light cycle (12 hours light and 12 hours dark); at room temperature: 72±8° F.; and at 30%-70% relative humidity. Fast the dogs for 16 hours prior to the start of the study, then dose the fasted dogs with vehicle (1% HEC, 0.25%, Tween 80, Antifoam) or one of the test compounds in that vehicle. Bleed the dogs one hour after dosing, (0.5 ml from the jugular vein) for a time 0 sample. Dose the dogs with olive oil (Sigma Catalog#: O-1514, 5 ml/kg) immediately after collection of the time 0 sample. Collect samples into an EDTA tube on ice at 1.5, 2, 3, 5, 7, and 9 hrs post compound/vehicle dosing. Centrifuge the samples at 9000 cpm for 15 min and analyze (Roche Cat no. 1877771) for plasma total triglyceride using a Roche Hitachi 917. For plasma TAG18.1_18.1_18.1 measurement, extract the samples and perform LC/MS/MS analysis similarly to that described above in MoGAT-2 Cell Assay using 10 μL of plasma.

The analyte is the [M+NH4]+ ion of TAG 18:1 18:1 18:1, which has a mass of 902.8 m/z; the internal standard is D5 TAG 16:0 16:0 16:0, which has a mass of 829.8 m/z. Report the ratio of the 603.5 m/z daughter ion of 902.8 m/z (TAG 18:1 18:1 18:1) and the 556.5 m/z daughter ion of 829.8 m/z (D5 TAG 16:0 16:0 16:0 internal standard) changes in TAG 18:1 18:1 18:1 relative amount. Calculate the net plasma TAG AUC from total TAG AUC minus baseline TAG AUC using Graphpad Prism4: (Net AUC$_{TAG}$=AUC$_{TAG}$ post oil bolus–AUC$_{TAG}$ at 0 hour). The percent inhibition of plasma triglyceride is calculated as follows: the (oil bolus group mean of net TAG AUC–oil bolus group mean of net TAG AUC with compound treatment/oil bolus group mean of net TAG AUC) *100. The final statistic analysis uses Dunnett's method of One way Anova for comparison with the control. All Net TAG AUC values are transformed to ranked averaged AUC for comparison to limit the variability within the studies. The ability of exemplified compounds of the present invention to inhibit MoGAT-2 activity and reduce TAG absorption in vivo can be further evaluated according to this assay.

Example 2 was evaluated in this model at 10 mg/kg dose. A statistically significant (p<0.05) reduction was observed for both parameters used to evaluate oil bolus-induced excursion of triglycerides in circulation. Results were as follows: 77% reduction in total triglycerides and 67% reduction in TAG 18.1_18.1_18.1.

The exemplified compounds of the present invention can be readily formulated into pharmaceutical compositions in accordance within accepted practices such as found in Remington's Pharmaceutical Sciences, Gennaro, Ed., Mack Publishing Co. Easton Pa. 1990.

A treating physician or other medical person will be able to determine an effective amount of the compound for treatment of a person in need, particularly for the treatment of hypertriglyceridemia. Preferred pharmaceutical compositions can be formulated as a tablet or capsule for oral administration. The tablet or capsule can include a compound of the present invention in an effective amount for treating a patient in need of treatment.

What is claimed is:

1. A compound of the formula below:

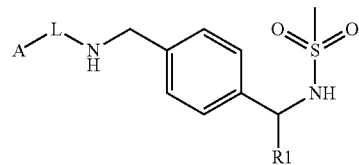

wherein
L is selected from: —CH₂—, and —CH₂CH₂—;
R1 is selected from: —CH₃ and —CF₃;
A is selected from:

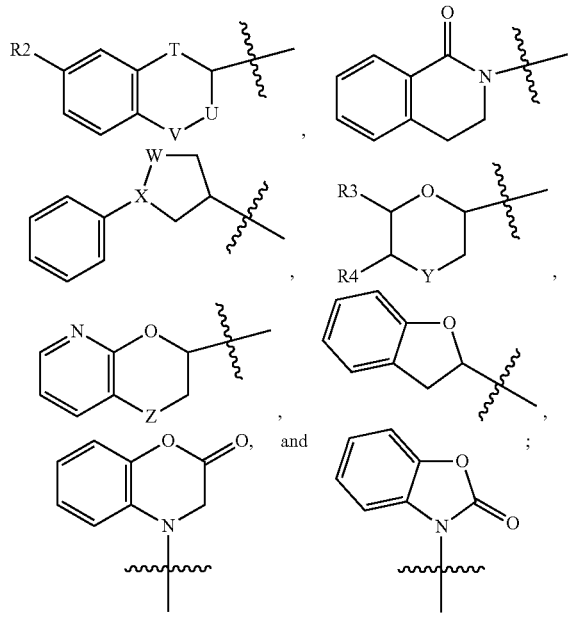

wherein,
T is selected from: CH₂, NH, and O;
U is selected from: CH₂, NH, and O;
V is selected from: CH₂, C=O, NH, N—CH₃, and O;
provided that at least one but not all of T, U, and V are CH₂, and when U is O then each of T and V is other than O or N;
W is selected from: CH₂ and O;
X is selected from: CH and N; provided that when W is CH₂, X is N and when W is O, X is CH;
Y is selected from: CH₂, N—C₆H₅, and O;
Z is selected from CH₂ and O:
R2 is selected from: H and halogen;
R3 is selected from: H, cyclopropyl, and phenyl;
R4 is selected from H and phenyl;
wherein ⸝ identifies the bond attaching A to L;
and pharmaceutically acceptable salts thereof.

2. A compound according to claim 1 which is:

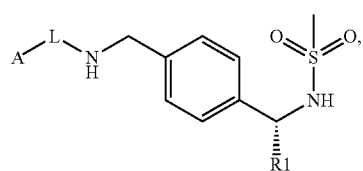

or a pharmaceutically acceptable salt thereof.

3. A compound according to claim 2 wherein L is —CH₂—.
4. A compound according to claim 3 wherein R1 is —CH₃.
5. A compound according to claim 3 wherein R1 is —CF₃.
6. A compound according to claim 5 wherein A is selected from:

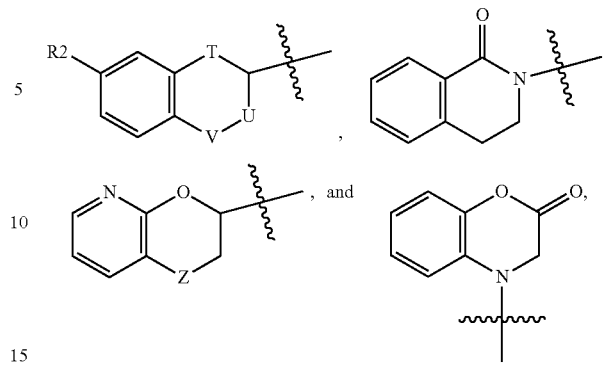

or a pharmaceutically acceptable salt thereof.

7. A compound according to claim 6 wherein A is

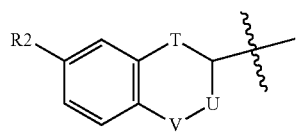

8. A compound according to claim 7 wherein;
T is O or N;
U is CH₂; and
V is O or N.

9. A compound according to claim 8 wherein T and V are both O.

10. A compound according to claim 8 wherein T is O and V is N.

11. A compound according to claim 7 wherein T and V are both CH₂ and U is O.

12. A compound according to claim 11 wherein R2 is H.

13. A compound according to claim 2 wherein A is selected from:

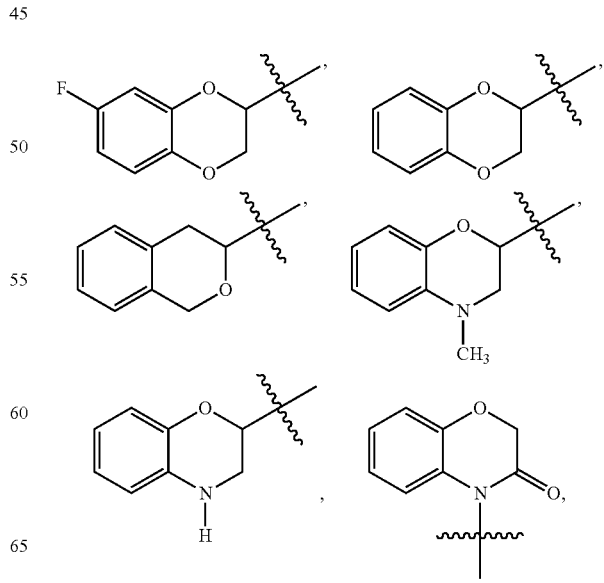

-continued

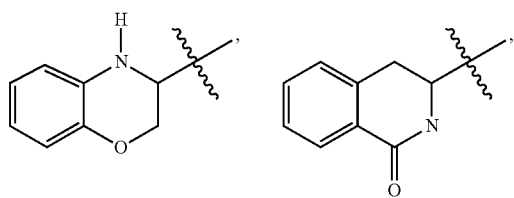

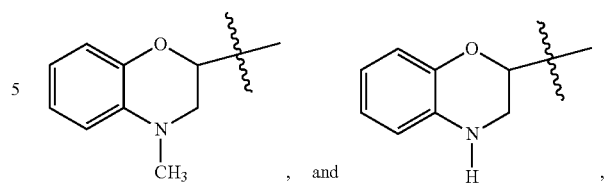, and or a pharmaceutically acceptable salt thereof.

18. A compound according to claim 2 wherein A is selected from:

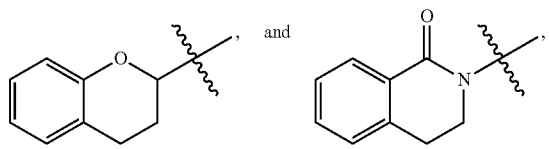, or a pharmaceutically acceptable salt thereof.

14. A compound according to claim 2 wherein A is selected from:

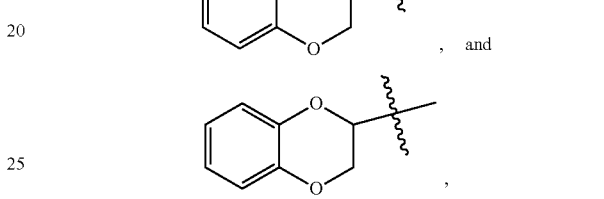

or a pharmaceutically acceptable salt thereof.

19. A compound of the formula below:

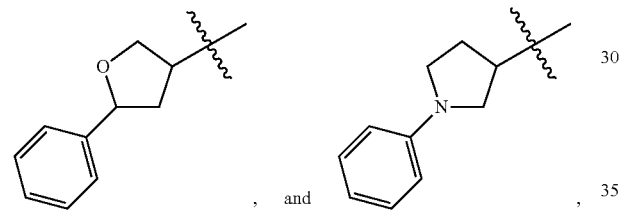, or a pharmaceutically acceptable salt thereof.

15. A compound according to claim 2 wherein A is selected from:

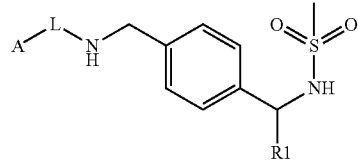

wherein

L is selected from: —CH$_2$—, and —CH$_2$CH$_2$—;

R1 is selected from: —CH$_3$ and —CF$_3$;

A is selected from:

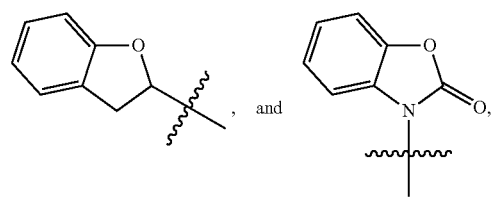 [SMILES: *C1Cc2ccccc2O1 ; *n1c(=O)oc2ccccc21], or a pharmaceutically acceptable salt thereof.

16. A compound according to claim 2 wherein A is selected from:

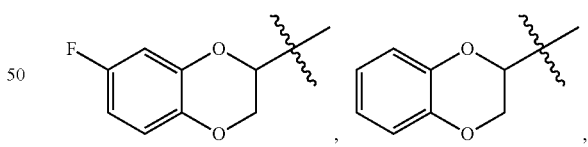

or a pharmaceutically acceptable salt thereof.

17. A compound according to claim 2 wherein A is selected from:

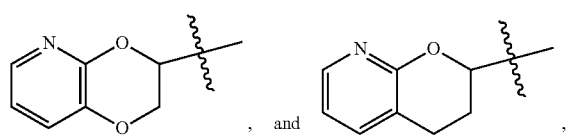 [SMILES: *C1COc2cccnc2O1 ; *C1CCc2cccnc2O1]

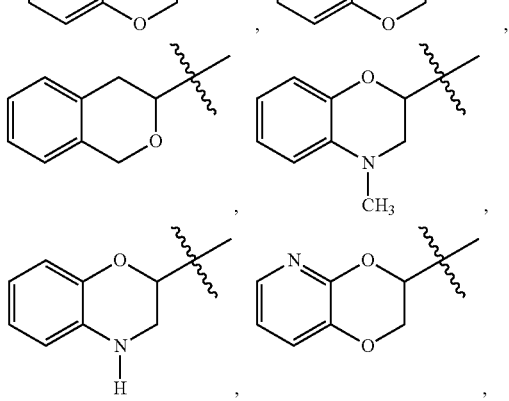

-continued

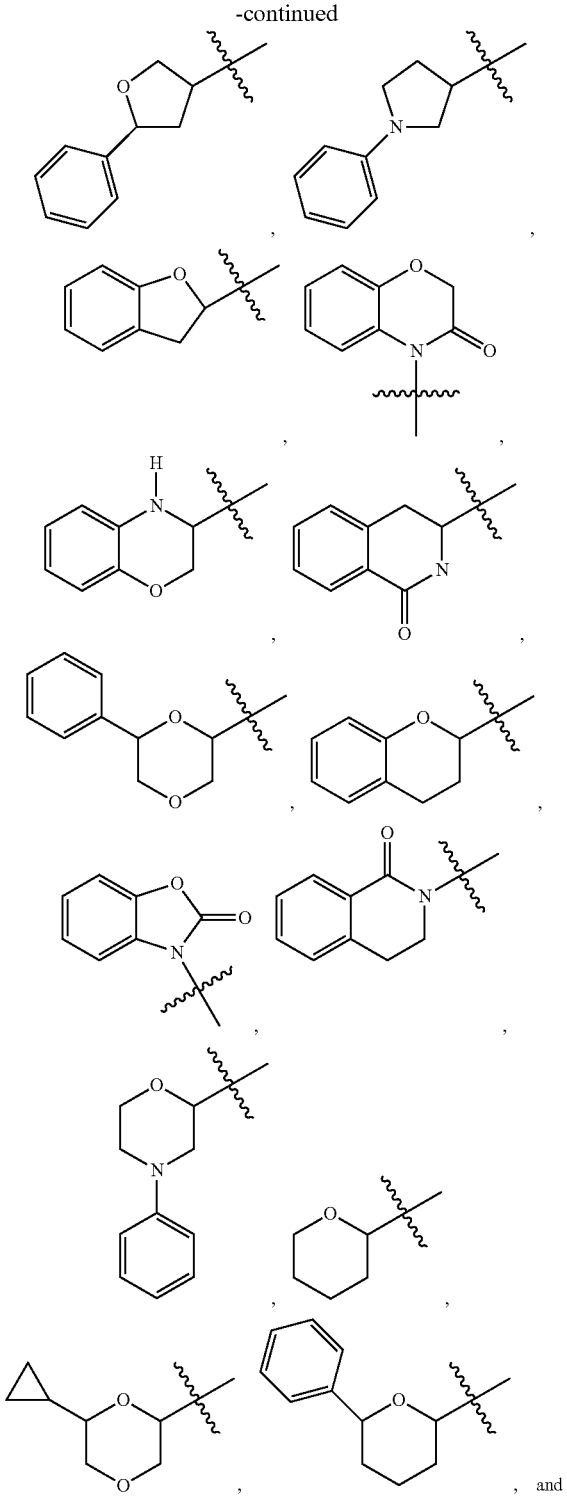

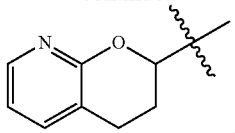

or a pharmaceutically acceptable salt thereof.

20. A compound according to claim 19 wherein A is selected from:

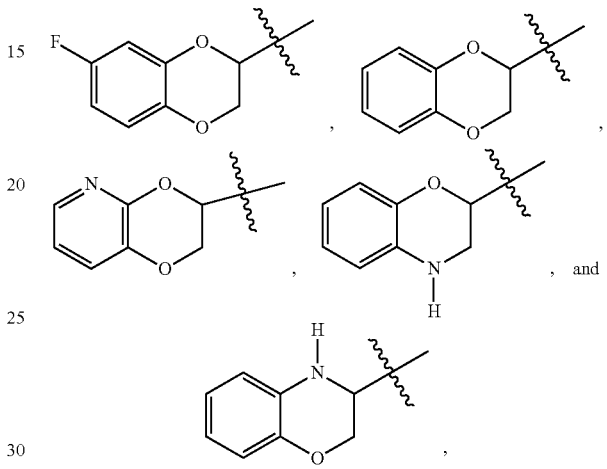

or a pharmaceutically salt thereof.

21. A compound according to claim 19 which is:

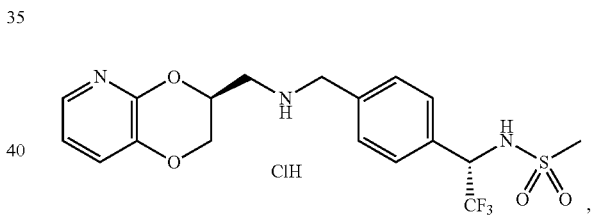

or a pharmaceutically salt thereof.

22. A pharmaceutical composition comprising a compound according to claim 2, or a pharmaceutically acceptable salt thereof, and at least one of a pharmaceutically acceptable carrier, diluent, or excipient.

23. A method of treating a patient in need of treatment for hypertriglyceridemia, the method comprises administering to the patient an effective amount of a compound according to claim 2, or a pharmaceutically acceptable salt thereof.

24. A pharmaceutical composition comprising a compound according to claim 21, or a pharmaceutically acceptable salt thereof, and at least one of a pharmaceutically acceptable carrier, diluent, or excipient.

* * * * *